United States Patent
Tokuyasu et al.

(10) Patent No.: US 6,331,650 B1
(45) Date of Patent: Dec. 18, 2001

(54) METHOD FOR MANUFACTURING AMINOALCOHOL

(75) Inventors: Jin Tokuyasu; Koichiro Isoue; Katsushi Nagareda; Takashi Onishi, all of Ibaraki (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 09/630,608

(22) Filed: Aug. 2, 2000

(30) Foreign Application Priority Data

| Aug. 3, 1999 | (JP) | 11-219794 |
| Aug. 3, 1999 | (JP) | 11-219795 |
| Sep. 27, 1999 | (JP) | 11-272146 |

(51) Int. Cl.$^7$ .................. C07C 211/00; C07D 307/02
(52) U.S. Cl. .................. 564/463; 549/424; 549/480
(58) Field of Search .................. 564/463; 549/424, 549/480

(56) References Cited

U.S. PATENT DOCUMENTS

| 2,516,337 | 7/1950 | Olin | 260/584 |
| 4,663,468 | 5/1987 | Tokitoh et al. | 549/273 |
| 4,808,737 | 2/1989 | Yoshimura et al. | 549/423 |
| 5,233,093 | 8/1993 | Pitchai et al. | 568/454 |
| 5,663,444 | 9/1997 | Melder et al. | 564/477 |
| 5,684,167 | 11/1997 | Omatsu et al. | 549/475 |

FOREIGN PATENT DOCUMENTS

| 857501 | 4/1952 | (DE) . |
| 196 02 049 | 7/1997 | (DE) . |
| 1 493 154 | 8/1975 | (GB) . |
| 60-019781 | 1/1985 | (JP) . |
| 64-009963 | 1/1989 | (JP) . |
| 3-261775 | 11/1991 | (JP) . |
| 3-261776 | 11/1991 | (JP) . |
| 6-166653 | 6/1994 | (JP) . |
| 11-090238 | 4/1999 | (JP) . |

OTHER PUBLICATIONS

C. Glacet, Bull. Soc. Chem. Fr., pp. 575–586, "Dérivés α–Amines de Tétrahydropyranne Et De Tétrahydrofurannes," 1954.

R. D. Westland, et al., Journal of Medicinal Chemistry, vol. 16, No. 4, pp. 319–327, "Antiradiation Agents. Substituted 2–Pyridyloxy and 2–Quinolyloxy Derivatives of S–2–(Alkylamino)Ehtyl Hydrogen Thiosulfates and 3–Alkylthiazolidines and Substituted 2–Pyridyloxy Derivatives of 2–(Alkylamino)Ethanethiols and Corresponding Disulfides," 1973.

J. Tesse, et al., C. R. Acad. Sc., vol. 280, pp. 1525–1528, "Étude Comformationnelle Par RMN D'α–Aminotétrahydropyrannes," Jun. 30, 1975.

C. Glacet, et al., Bull. Soc. Chem. Fr., pp. 224–228, "Préparation et Propriétés De L'A–Butylamino Tétrahydropyranne Et De L'A–Diéthylamino Tétrahydropyranne," 1955.

G. E. McCasland, et al., Journal of Organic Chemistry, vol. 22, pp. 122–126, "Synthesis of 3,4–Dimethyl Spirobipyrrolidinium Salts By Cyclization Of Pyrrolidinealkanols," 1957.

P. Štern, et al., Collection Czechoslov. Chem. Commun., vol. 39, pp. 3538–3547, "On Hydroboration of 5–Dimethylamino–3–Methyl–1–Pentene and 5–Dimethylamino–3,3–Dimethyl–1–Pentene," 1974.

C. Glacet, et al., Bull. Soc. Chem. Fr., pp. 2097–2102, "Préparation D'α–Aminoépoxydes Complexes ES D'Amines Polyhydroxylées," 1962.

W. G. Stoll, et al., Helvitica Chimica Acta, vol. XXXIII, No. V, pp. 1208–1217, "Anitihistaminica III. Über α–(Aminoalkyl)–Stilbene," 1950.

Carl D. Lunsford, et al., "Preparation of 4–Amino–1–Butanols and Some Derivatives Of Pharmacological Interest," J. Org. Chem., vol. 22, 1957, pp. 1225–1228.

Roger Adams, et al., The Absolute Configuration Of The C₁Atom In Retronecanone (1–Methyl–7–Oxopyrrolizidine), J. Am. Chem. Soc., vol. 81, 1959, pp. 4946–4951.

Robert V. Hoffman, et al., "Addition–Rearrangement Reactions of N–(Arylsulphonyloxy)Amines and 3,4–Dihydro–2H–Pyran," J. Chem. Soc. Perkin Trans. I, 1989, pp. 1375–1380.

*Primary Examiner*—Amelia Owens
(74) *Attorney, Agent, or Firm*—Oblon, Spivak, McClelland, Maier & Neustadt, P.C.

(57) ABSTRACT

An aminoalcohol is synthesized by reacting a cyclic hemiacetal expressed by Formula 1

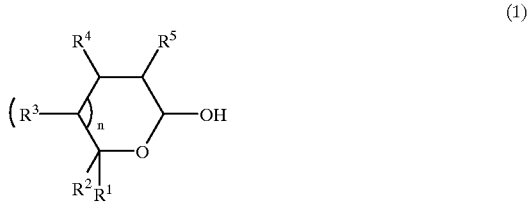

(1)

(where n is 0 or 1; $R^1$ and $R^2$ are each a hydrogen atom, a monovalent saturated hydrocarbon group which is optionally substituted, or a monovalent aromatic group which is optionally substituted, or $R^1$ and $R^2$ are bonded together into a divalent saturated hydrocarbon group which is optionally substituted; and $R^3$, $R^4$, and $R^5$ are each a hydrogen atom, a monovalent saturated hydrocarbon group which is optionally substituted, or a monovalent aromatic group which is optionally substituted), with hydrogen and any one of ammonia, a primary amine and secondary amine in the presence of a hydrogenation catalyst.

15 Claims, No Drawings

METHOD FOR MANUFACTURING AMINOALCOHOL

BACKGROUND OF THE INVENTION

1. Field of the Invention

The present invention relates to a method for manufacturing an aminoalcohol. More particularly the present invention relates to a method for manufacturing an aminoalcohol, classified as a tertiary amine, in which one or more of the three substituents bonded to the nitrogen atom of the amino group are carbon-skeleton organic group(s) (such as alkylene group(s)) which have four or five carbon atoms in their carbon-skeleton(s) and link hydroxyl group(s) to the nitrogen atom of the amino group. The present invention also relates to a method for manufacturing an aminoalcohol, classified as a primary or secondary amine, in which the substituent(s) bonded to the nitrogen atom of the amino group are carbon-skeleton organic group(s) (such as alkylene group(s)) which have four or five carbon atoms in their carbon-skeleton(s) and link hydroxyl group(s) to the nitrogen atom of the amino group.

2. Description of the Related Art

Ethanolamines such as 2-(dimethylamino)ethanol, 2-(diethylamino)ethanol, and 2-(dibutylamino)ethanol are currently being manufactured industrially as aminoalcohols classified as tertiary amines. N-alkyldiethanolamines, triethanolamine, and other such ethanolamines are also aminoalcohols that can be used industrially at the present time. These ethanolamines are synthesized by reacting an alkylamine or ammonia and ethylene oxide (see, for example, U.S. Pat. No. 5,663,444).

Of the aminoalcohols classified as tertiary amines, those other than ethanolamines are not manufactured industrially, but there are reports of methods for synthesizing 4-(dimethylamino)-1-butanol, for example, such as the following (i) and (ii).

(i) It is stated in the Journal of Organic Chemistry (22, 1225 (1957)) that 4-(dimethylamino)-1-butanol is obtained by putting γ-butyrolactone and dimethylamine in a sealed tube and reacting them for 4 hours at 150° C. to form N,N-dimethyl-γ-hydroxybutylamide, and then reacting this with lithium aluminum hydride in an ether solvent.

(ii) It is stated in the specification of West German Patent No. 857501 that 4-(dimethylamino)-1-butanol is obtained by allowing lithium aluminum hydride to act on N,N-dimethylsuccinamic acid.

Of the aminoalcohols classified as primary amines, examples of compounds being manufactured industrially at present include 2-aminoethanol and 3-amino-1-propanol. The former (2-aminoethanol) is manufactured by reacting ethylene oxide and ammonia (eg, Japanese Patent Application Laid-Open No. H11-90238), while the latter (3-amino-1-propanol) is manufactured by reducing 3-hydroxypropiononitrile in the presence of a Raney nickel catalyst or the like (eg, Japanese Patent Application Laid-Open No. S64-9963).

Of the aminoalcohols classified as secondary amines, examples of compounds being manufactured industrially include ethanolamines such as 2-(methylamino)ethanol. Ethanolamines such as these are manufactured by reacting an alkylamine with ethylene oxide.

However, with the above-mentioned methods for synthesizing ethanolamines classified as tertiary amines, because the number of carbon atoms in the ring of the raw material ethylene oxide is 2, it follows that the number of carbon atoms in the main chain of the alkylene groups between the amino groups and hydroxyl groups in the resulting aminoalcohol is limited to 2.

Synthesis methods such as the above-mentioned (i) and (ii) have been reported for aminoalcohols in which there are three or more carbon atoms in the main chain of the alkylene groups between the hydroxyl groups and the nitrogen atoms of the amino groups, but when viewed from an industrial standpoint, all of these methods have drawbacks in terms of the reaction raw materials, reaction time, treatment after the reaction, reaction equipment, and so forth. For instance, the above-mentioned methods (i) and (ii) both entail the use of lithium aluminum hydride, which has low handleability and is expensive, so they are hardly industrially advantageous methods.

Also, because of limitations imposed by the raw materials used or the reaction route, the number of carbon atoms in the main chain of the alkylene groups between the nitrogen atoms of the amino groups and the hydroxyl groups of the above-mentioned aminoalcohols classified as primary or secondary amines is necessarily limited to 2 or 3 for the former and 2 for the latter.

Therefore, the problem with the above ways of manufacturing an aminoalcohol with four or more (and particularly 4 or 5) carbon atoms between the hydroxyl group and the nitrogen atom of the amino group was that industrial manufacture was unfeasible.

By the way, 4-amino-2-methyl-1-butanol or 5-(methylamino)-1-pentanol has been reported as an aminoalcohol that is classified as a primary amine or secondary amine, that has 4 or 5 carbon atoms in the main chain of the alkylene group between the hydroxyl group and the nitrogen atom of the amino group, and that has been synthesized in the laboratory. Specifically, the former has been synthesized in the laboratory by reacting 2-methyl-4-aminobutyric acid with lithium aluminum hydride in a tetrahydrofuran solvent for 6 hours under reflux conditions (J. Amer. Chem. Soc., 81, 4946 (1959)). The latter has been synthesized in the laboratory by mixing hydrochloric acid and dihydropyran, then adding an aqueous methylamine solution to this mixture, extracting and condensing the crude reaction solution thus obtained, then reacting this product with sodium borohydride in an ethanol solvent, in the isolated yield of 21% based on the dihydropyran (J. Chem. Soc. Perkin Trans. I, 1375 (1989)). Therefore, it may be supposed that these experimental manufacturing processes could be applied to industrial manufacture.

These experimental manufacturing processes can hardly be considered industrially advantageous methods, however, because they require the use of lithium aluminum hydride, dihydropyran, sodium borohydride, and other such expensive reaction raw materials, the reaction raw materials have low handleabilities, the treatment after the reaction is troublesome, and new reaction equipment has to be installed.

SUMMARY OF THE INVENTION

It is a first object of the present invention to provide a method for manufacturing an aminoalcohol classified as a tertiary amine, in which aminoalcohol one of the three substituents bonded to the nitrogen atom of the amino group is a carbon-skeleton organic group (such as an alkylene group) which has four or five carbon atoms in the carbon-skeleton and links hydroxyl group to the nitrogen atom of the amino group, with which method the aminoalcohol can be manufactured industrially advantageously.

It is a second object of the present invention to provide a method for manufacturing an aminoalcohol classified as a tertiary amine, in which aminoalcohol two or more of the three substituents bonded to the nitrogen atom of the amino group are carbon-skeleton organic groups (such as alkylene groups) which have four or five carbon atoms in the carbon-skeletons and link hydroxyl groups to the nitrogen atoms of the amino groups, with which method the aminoalcohol can be manufactured industrially advantageously.

It is a third object of the present invention to provide a method for manufacturing an aminoalcohol classified as a primary or secondary amine, in which aminoalcohol the substituent bonded to the nitrogen atom of the amino group are a carbon-skeleton organic group (such as an alkylene group) which has four or five carbon atoms in the carbon-skeleton and link hydroxyl group to the nitrogen atom of the amino group, with which method the aminoalcohol can be manufactured industrially advantageously.

The first object of the present invention is achieved by the following manufacturing method A or manufacturing method B, the second object is achieved by the following manufacturing method C or manufacturing method D, and the third object is achieved by the following manufacturing method E or manufacturing method F.

Specifically, manufacturing method A of the present invention is a method for manufacturing an aminoalcohol expressed by Formula 3a

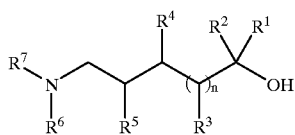

(3a)

(where n is 0 or 1; $R^1$ and $R^2$ are each a hydrogen atom, a monovalent saturated hydrocarbon group which is optionally substituted, or a monovalent aromatic group which is optionally substituted, or $R^1$ and $R^2$ are bonded together into a divalent saturated hydrocarbon group which is optionally substituted; $R^3$, $R^4$, and $R^5$ are each a hydrogen atom, a monovalent saturated hydrocarbon group which is optionally substituted, or a monovalent aromatic group which is optionally substituted; and $R^6$ and $R^7$ are each a monovalent saturated hydrocarbon group which is optionally substituted or a monovalent aromatic group which is optionally substituted, or $R^6$ and $R^7$ are bonded together into a divalent saturated aliphatic group which is optionally substituted), which method comprises:

reacting a cyclic hemiacetal expressed by Formula 1:

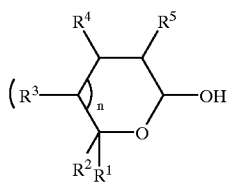

(1)

(where n, $R^1$, $R^2$, $R^3$, $R^4$ and $R^5$ are defined the same as above),
with hydrogen and a secondary amine expressed by Formula 2a

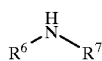

(2a)

(where $R^6$ and $R^7$ are defined the same as above),
in the presence of a hydrogenation catalyst to obtain the aminoalcohol expessed by Formula 3a.

Manufacturing method B of the present invention is a method for manufacturing an aminoalcohol expressed by Formula 3a, which method comprises:

reacting a cyclic hemiacetal expressed by Formula 1 with a secondary amine expressed by Formula 2a to obtain an aminoether expressed by Formula 4a

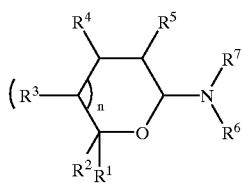

(4a)

(where n, $R^1$, $R^2$, $R^3$, $R^4$, $R^5$, $R^6$ and $R^7$ are defined the same as above); and hydrogenating the aminoether to obtain the aminoalcohol expressed by Formula 3a.

Manufacturing method C of the present invention is a method for manufacturing an aminoalcohol expressed by Formula 3b

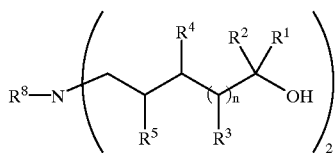

(3b)

(where n, $R^1$, $R^2$, $R^3$, $R^4$ and $R^5$ are defined the same as above, and $R^8$ is a monovalent saturated hydrocarbon group which is optionally substituted or a monovalent aromatic group which is optionally substituted), which method comprises:

reacting a cyclic hemiacetal expressed by Formula 1 with hydrogen and a primary amine expressed by Formula 2b

$R^8$—$NH_2$ (2b)

(where $R^8$ is defined the same as above),
in the presence of a hydrogenation catalyst to obtain the aminoalcohol expressed by Formula 3b.

Manufacturing method D of the present invention is a method for manufacturing an aminoalcohol expressed by Formula 3b, which method comprises:

reacting a cyclic hemiacetal expressed by Formula 1 with a primary amine expressed by Formula 2b; and subjecting the reaction mixture thus obtained to a hydrogenation reaction to obtain the aminoalcohol expressed by Formula 3b.

Manufacturing method E of the present invention is a method for manufacturing an aminoalcohol expressed by Formula 3c

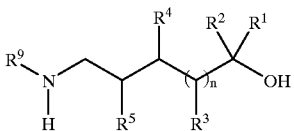

(3c)

(where n, $R^1$, $R^2$, $R^3$, $R^4$ and $R^5$ are defined the same as above, and $R^9$ is a hydrogen atom, a monovalent saturated hydrocarbon group which is optionally substituted or a monovalent aromatic group which is optionally substituted), which method comprises:

reacting a cyclic hemiacetal expressed by Formula 1

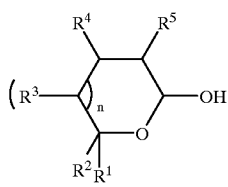

(1)

(where n, $R^1$, $R^2$, $R^3$, $R^4$ and $R^5$ are defined the same as above),
with hydrogen and a nitrogen-containing compound expressed by Formula 2c $$R^9\text{—}NH_2 \qquad (2c)$$

(where $R^9$ is defined the same as above),
in the presence of a hydrogenation catalyst to obtain the aminoalcohol expressed by Formula 3c.

Manufacturing method F of the present invention is a method for manufacturing an aminoalcohol expressed by Formula 3c, which method comprises:

reacting a cyclic hemiacetal expressed by Formula 1 with a nitrogen-containing compound expressed by Formula 2c; and subjecting the reaction mixture thus obtained to reaction with hydrogen in the presence of a hydrogenation catalyst obtain the aminoalcohol expressed by Formula 3c.

DETAILED DESCRIPTION OF THE INVENTION

The present invention will now be described in detail.

The above-mentioned manufacturing methods A and B of the present invention are similar in that they both make use of the cyclic hemiacetal of Formula 1 and the secondary amine of Formula 2a as the main raw materials, and the target substance is the aminoalcohol of Formula 3a, which is classified as a tertiary amine.

In Formula 1, which represents the cyclic hemiacetal that is one of the raw materials, $R^1$ and $R^2$ are each a hydrogen atom, a monovalent saturated hydrocarbon group which is optionally substituted, or a monovalent aromatic group which is optionally substituted, or $R^1$ and $R^2$ are bonded together into a divalent saturated hydrocarbon group which is optionally substituted; and $R^3$, $R^4$, and $R^5$ are each a hydrogen atom, a monovalent saturated hydrocarbon group which is optionally substituted, or a monovalent aromatic group which is optionally substituted.

Examples of the monovalent saturated hydrocarbon groups which are optionally substituted, that may be expressed by $R^1$, $R^2$, $R^3$, $R^4$ and $R^5$, include alkyl groups having no substituent, such as a methyl group, an ethyl group, a propyl group, an isopropyl group, a butyl group, and an isobutyl group; cycloalkyl groups having no substituent, such as a cyclopentyl group, a cyclohexyl group, a 2-methylcyclohexyl group, and a cyclooctyl group; and a substituted alkyl groups or a substituted cycloalkyl groups having a chemical structure in which at least one of the hydrogen atoms of the alkyl groups or cycloalkyl groups listed above has been substituted with an alkoxy group, a formyl group protected in acetal form, a hydroxyl group, or the like. Examples of the monovalent aromatic groups which are optionally substituted, that may be expressed by $R^1$, $R^2$, $R^3$, $R^4$, and $R^5$, include aryl groups having no substituent, such as a phenyl group, a tolyl group and a naphthyl group; aromatic heterocyclic groups having no substituent, such as a pyridyl group; aralkyl groups having no substituent, such as a benzyl group; and substituted aryl groups, substituted, aromatic heterocyclic groups, or substituted aralkyl groups having a chemical structure in which at least one of the hydrogen atoms of the aryl groups, aromatic heterocyclic groups, or aralkyl groups listed above has been substituted with an alkoxy group, a formyl group protected in acetal form, a hydroxyl group, or the like.

Examples of divalent saturated hydrocarbon groups which are optionally substituted, that may be expressed in a form in which $R^1$ and $R^2$ in Formula 1 are bonded together, include alkylene groups having no substituent, such as an ethylene group, a tetramethylene group, and a pentamethylene group; and substituted alkylene groups having a chemical structure in which at least one of the hydrogen atoms of the above alkylene groups having no substitutent has been substituted with an alkoxy group, a formyl group protected in acetal form, a hydroxyl group, or the like. It is preferable for the number of carbon atoms in the main chain interposed between two bonds in the divalent saturated hydrocarbon group which is optionally substituted (excluding carbon atoms in side chains) to be between 2 and 11.

In Formula 1 expressing the cyclic hemiacetal, n is 0 or 1. When n is 0, the cyclic hemiacetal of Formula 1 has the structure of a five-member ring (that is, a tetrahydrofuran ring), and when n is 1, the cyclic hemiacetal has the structure of a six-member ring (that is, a tetrahydropyran ring).

Specific examples of the cyclic hemiacetal of Formula 1 include 2-hydroxytetrahydropyran, 2-hydroxy-3-methyltetrahydropyran, 2-hydroxy-4-methyltetrahydropyran, 2-hydroxy-5-methyltetrahydropyran, 2-hydroxy-6-methyltetrahydropyran, 2-hydroxy-6-isobutyl-4-methyltetrahydropyran, 2-hydroxy-1-oxaspiro[5.5]undecane, and other such pyran compounds; and 2-hydroxytetrahydrofuran, 2-hydroxy-3-methyltetrahydrofuran, 2-hydroxy-4-methyltetrahydrofuran, 2-hydroxy-5-methyltetrahydrofuran, 3-ethyl-2-hydroxytetrahydrofuran, 5,5-dimethyl-2-hydroxytetrahydrofuran, 3,4-dimethyl-2-hydroxytetrahydrofuran, 3,5-dimethyl-2-hydroxytetrahydrofuran, 2-hydroxy-5-methyl-5-(4-methylpentyl)tetrahydrofuran, 2-hydroxy-3-(hydroxymethyl)tetrahydrofuran, 5-cyclohexyl-2-hydroxytetrahydrofuran, 1-oxa-2-hydroxyspiro[4.5]decane, and other such furan compounds.

The above-mentioned cyclic hemiacetal can be synthesized by a known method, but a method for synthesizing a cyclic hemiacetal by subjecting an alkenol compound of Formula 5

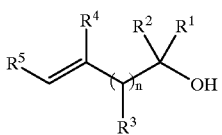

(5)

(where n, $R^1$, $R^2$, $R^3$, $R^4$ and $R^5$ are defined the same as above, and the configuration related to the carbon-carbon double bond is an E or Z configuration), to hydroformylation reaction is particularly favorable because it makes inexpensive manufacture possible on an industrial scale. Specific examples of alkenol compounds when n is 1 in Formula 5 include 1-buten-4-ol, 3-penten-1-ol, 2-methyl-1-buten-4-ol, 3-methyl-1-buten-4-ol, 1-penten-4-ol, 4-methyl-1-penten-4-ol, 2,6-dimethyl-1-hepten-4-ol, 4-cyclohexyl-1-buten-4-ol, 1-(2-propenyl)-1-cyclohexanol, and other such 1-buten-4-ol compounds. Specific examples of alkenol compounds when n is 0 in Formula 5 include 1-propen-3-ol, 2-methyl-1-propen-3-ol, 1-buten-3-ol, 3-methyl-1-buten-3-ol, 2-buten-1-ol, 2-butene-1,4-diol, 2-methyl-2-buten-1-ol, 3,7-dimethyl-1-octen-3-ol, 3 -cyclohexyl-1-propen-3-ol, 1-vinyl-1-cyclohexanol, and other such 1-propen-3-ol compounds.

A variety of known reaction methods can be employed for the hydroformylation of the alkenol compound of Formula 5. For example, it is possible to use a method comprising the reaction of this alkenol compound with hydrogen and carbon monoxide in the presence of a rhodium compound and a tertiary organophosphorus compound. Examples of known reaction methods are the methods for hydroformylating 2-methyl-1-buten-4-ol discussed in U.S. Pat. No. 4,663,468, U.S. Pat. No. 4,808,737 and elsewhere. Also, methods for hydroformylating allyl alcohol are discussed in G.B. Patent No. 1,493,154 and Japanese Patent Application Laid-Open No. H3-261775, U.S. Pat. No. 5,233,093, Japanese Patent Application Laid-Open No. H6-166653 and elsewhere. When a cyclic hemiacetal obtained by the hydroformylation of one of these alkenol compounds is used as a raw material in the present invention, it can be a refined cyclic hemiacetal obtained by subjecting the reaction mixture obtained by hydroformylation to distillation, recrystallization, or other such separation and refinement, but it can also be used in the form of the hydroformylation reaction mixture containing the cyclic hemiacetal, rhodium compound, tertiary organophosphorus compound, reaction by-products, and so forth, or it can be a crude cyclic hemiacetal obtained by subjecting this reaction mixture to a simple separation process.

In Formula 2a expressing the secondary amine that is one of the raw materials, $R^6$ and $R^7$ are each a monovalent saturated hydrocarbon group which is optionally substituted or a monovalent aromatic group which is optionally substituted, or $R^6$ and $R^7$ are bonded together into a divalent saturated aliphatic group which is optionally substituted.

Examples of the monovalent saturated hydrocarbon groups, which are optionally substituted, that may be expressed by $R^6$ and $R^7$, here include alkyl groups having no substituent, such as a methyl group, an ethyl group, a propyl group, a butyl group, an isobutyl group, an octyl group and 2-ethylhexyl group; cycloalkyl groups having no substituent, such as a cyclohexyl group, a 2-methylcyclohexyl group, and a cyclooctyl group; and substituted alkyl groups (such as the 2-hydroxyethyl group or 2-hydroxypropyl group) or substituted cycloalkyl groups having a chemical structure in which at least one of the hydrogen atoms of the alkyl groups or cycloalkyl groups listed above has been substituted with an alkoxy group, a formyl group protected in acetal form, a hydroxyl group, or the like. Examples of the monovalent aromatic groups which are optionally substituted, that may be expressed by $R^6$ and $R^7$, include aryl groups having no substituent, such as a phenyl group, a tolyl group, and a naphthyl group; aralkyl groups having no substituent, such as a benzyl group; and substituted aryl groups or substituted aralkyl groups having a chemical structure in which at least one of the hydrogen atoms of the aryl groups or aralkyl groups listed above has been substituted with an alkoxy group, a formyl group protected in acetal form, a hydroxyl group, or the like. It is preferable for the number of carbons contained in these aromatic groups to be between 6 and 14.

Examples of the divalent saturated hydrocarbon groups which are optionally substituted, that may be expressed in a form in which $R^6$ and $R^7$ in Formula 2a are bonded together, include alkylene groups having no substituent, such as an ethylene group, a tetramethylene group, a pentamethylene group, a methylpentamethylene group, and a 1,5-hexanediyl group; hetero atom-containing alkylene groups having no substituent, such as a 3-oxapentamethylene group ($—CH_2CH_2OCH_2CH_2—$) or a 3-aza-3-methylpentamethylene group ($—CH_2CH_2N(CH_3)CH_2CH_2—$); and substituted alkylene groups or substituted hetero atom-containing alkylene groups having a chemical structure in which at least one of the hydrogen atoms of the above alkylene groups or hetero atom-containing alkylene groups has been substituted with an alkoxy group, a formyl group protected in acetal form, a hydroxyl group, a pyrimidinyl group, or the like. It is preferable for the number of atoms in the main chain interposed between two bonds in the divalent saturated hydrocarbon group which is optionally substituted (excluding atoms in side chains) to be between 2 and 11.

Specific examples of the secondary amine of Formula 2a include dimethylamine, diethylamine, diisopropylamine, dipropylamine, diisobutylamine, dibutylamine, dioctylamine, di(2-ethylhexyl)amine, dicyclohexylamine, N-methylcyclohexylamine, diphenylamine, N-methylaniline, N-methyl-o-toluidine, N-methyl-m-toluidine, N-methyl-p-toluidine, N-methyl-α-naphthylamine, N-phenyl-α-naphthylamine, N-methylbenzylamine, dibenzylamine, diethanolamine, N-methylethanolamine, diisopropanolamine, N-methylisopropanolamine, and other such acyclic amines; and aziridine, pyrrolidine, piperidine, 2-pipecoline, 3-pipecoline, 4-pipecoline, morpholine, N-methylpiperazine, 1-(2-hydroxyethyl)piperazine, 2-(1-piperazinyl)pyrimidine, and other such cyclic amines.

The secondary amine of Formula 2a used in the reaction according to manufacturing method A or B may be in the form of a salt. Examples of salts that can be used include salts formed from a secondary amine and hydrochloric acid, sulfuric acid, nitric acid, acetic acid, propionic acid, or another such protic acid. A typical example of such a salt is dimethylammonium chloride.

Next, manufacturing method A of the present invention will be described in detail.

The proportions in which the cyclic hemiacetal of Formula 1 and the secondary amine of Formula 2a (or salt thereof) are used in manufacturing method A are not necessarily limited. However, because this cyclic hemiacetal is an equivalent of an aldehyde, in its reaction with the secondary amine and hydrogen, there is the possibility that it will be hydrogenated without reacting with the secondary amine, and the possibility that it will undergo self-condensation. These side reactions make the process less cost-effective, so to suppress side reactions, the amount in which the above secondary amine is used should be between 0.9 and 30 moles, and preferably between 1 and 5 moles, per mole of the above-mentioned cyclic hemiacetal being used.

In supplying the secondary amine of Formula 2a (or a salt thereof) to the reaction system in the reaction according to manufacturing method A, the form of the secondary amine is not necessarily limited, and the secondary amine may be supplied just as it is, or it may first be diluted with a solvent. Specific examples of solvents for diluting the secondary amine include water, methanol, ethanol, propanol, diethyl ether, tetrahydrofuran, dioxane, pentane, hexane, cyclohexane, benzene, toluene, and xylene. These solvents can be used singly or in mixtures of two or more types. When a salt of a secondary amine and a protic acid is used as the secondary amine, better results may be obtained if a basic compound is present in the reaction system. Specific examples of this basic compound include lithium hydroxide, sodium hydroxide, potassium hydroxide, lithium acetate, sodium acetate, potassium acetate, triethylamine, tributylamine, trioctylamine, and pyridine. When this basic compound is used, the amount in which it is used is usually no more than 10 moles, and preferably no more than 2 moles, per mole of the salt of a secondary amine.

The reaction in manufacturing method A involves reacting the cyclic hemiacetal of Formula 1 with the secondary amine of Formula 2a and hydrogen in the presence of a hydrogenation catalyst. Any catalyst that is generally used in catalytic hydrogenation reactions can be used as this hydrogenation catalyst, examples of which include catalysts whose active component is a metal such as palladium, rhodium, nickel, or platinum. This hydrogenation catalyst can be in the form of the metal itself that serves as the active component; an oxide of this metal; an alloy of this metal with another metal; a carried catalyst in which the metal (or oxide or alloy) that serves as the active component is carried on activated charcoal, alumina, silica gel, diatomaceous earth, or another such carrier; or the like. The amount in which the hydrogenation catalyst is used is not necessarily limited, but is usually between 0.0001 and 0.2 weight part per weight part of the cyclic hemiacetal of Formula 1. From the standpoints of reaction rate and the cost of manufacturing the targeted aminoalcohol, it is preferable for this amount to be between 0.005 and 0.1 weight part per weight part of the cyclic hemiacetal of Formula 1.

The use of a solvent is not necessarily required in the reaction of manufacturing method A, but a solvent may be used, so long as it has no adverse effect on the reaction in question. Solvents that can be used include water; methanol, ethanol, propanol, and other alcohol solvents; diethyl ether, tetrahydrofuran, dioxane, and other ether solvents; and pentane, hexane, cyclohexane, benzene, toluene, xylene, and other hydrocarbon solvents. These can be used singly or in mixtures of two or more types. When a solvent is used, the amount in which it is used is usually between 0.1 and 10 weight parts per weight part of the cyclic hemiacetal of Formula 1.

In the reaction in manufacturing method A, hydrogen is brought into contact with a mixture containing the cyclic hemiacetal of Formula 1, the secondary amine of Formula 2a, and the hydrogenation catalyst. Examples of the form of this contact include having hydrogen gas be present in the atmosphere of the reaction system in which this mixture is present, and introducing (bubbling) hydrogen gas into the mixture. The partial pressure of the hydrogen in the reaction system is not necessarily limited, but is usually between 0.5 and 100 atm (absolute pressure). As long as there is no adverse effect on the reaction in question, a gas other than hydrogen (such as nitrogen or argon) may be contained in the gas phase of the reaction system.

The reaction temperature is not necessarily limited in the reaction of manufacturing method A, but a temperature between 20 and 180° C. is usually employed, and from the standpoints of a high reaction rate and a high selectivity to the targeted aminoalcohol, it is preferable to employ a temperature between 40 and 140° C.

The required reaction time is not necessarily limited in the reaction of manufacturing method A, and the reaction time (the residence time in the case of a continuous reaction process) can be appropriately set on the basis of the conversion of the cyclic hemiacetal and/or the selectivity to the produced aminoalcohol, as determined by a quantitative analysis means such as gas chromatography. Usually, though, the time is between 0.5 and 20 hours.

A variety of opperations can be employed as desired for conducting the reaction of manufacturing method A. This reaction can be conducted without the use of any special apparatus (such as an autoclave). For example, the reaction can be conducted by batch, semi-batch, or continuous process by using a general-purpose apparatus to mix the cyclic hemiacetal of Formula 1, the secondary amine of Formula 2a (or a salt thereof), and the hydrogenation catalyst by stirring or another such means under a hydrogen gas atmosphere and under the required temperature and hydrogen pressure. There are no particular restrictions on the order or rate at which the various components are mixed in the reaction, and the reaction may be commenced after all of the liquid or solid components supplied to the reaction (namely, the cyclic hemiacetal, secondary amine, and hydrogenation catalyst) have been mixed at once, or the reaction may be conducted while either the cyclic hemiacetal or the secondary amine is added to the reactor wherein the other component has been supplied along with the hydrogenation catalyst. In the latter case, part of components can be added during the reaction in a variety of forms, such as continuous addition, or intermittent addition that is divided up into a plurality of batches.

When a means is chosen such that the secondary amine of Formula 2a will be present in the reaction system in a proportion that is a large excess with respect to the cyclic hemiacetal of Formula 1 over most of the time during the reaction, side reactions such as those brought about by self-condensation of the cyclic hemiacetals can be suppressed, allowing the yield and selectivity of the targeted aminoalcohol to be higher. In this respect, a semi-batch reaction process comprising conducting the reaction while adding the cyclic hemiacetal to a mixture of the secondary amine and the hydrogenation catalyst, a continuous reaction process comprising conducting the reaction while the cyclic hemiacetal, secondary amine, and hydrogenation catalyst are continuously supplied to the reaction system and part of the reaction mixture is continuously taken out from the reaction system, or the like is preferred.

Upon completion of the reaction of manufacturing method A, the aminoalcohol of Formula 3a that is the targeted substance can be obtained at a high purity by, for example, removing the hydrogenation catalyst from the obtained reaction mixture by filtration, centrifugation, or the like, and then subjecting the resulting mixture to distillation, crystallization, column chromatography, or another such separation and purification process. Unreacted secondary amine can be recovered for reuse.

Next, manufacturing method B of the present invention will be described in detail.

Manufacturing method B includes a step of manufacturing the aminoether of Formula 4a by a reaction between the cyclic hemiacetal of Formula 1 and the secondary amine of Formula 2a, and a step of manufacturing the aminoalcohol of Formula 3a by the hydrogenation of this aminoether.

Except for the fact that there is no need for hydrogen or a hydrogenation catalyst, the reaction between the cyclic hemiacetal of Formula 1 and the secondary amine of Formula 2a according to manufacturing method B can be conducted in substantially the same manner as the reaction of the cyclic hemiacetal of Formula 1 with the secondary amine of Formula 2a and hydrogen in the presence of a hydrogenation catalyst according to manufacturing method A. Specifically, the two reactions share the same conditions for the proportions in which the cyclic hemiacetal and secondary amine (or salt thereof) are used, the form in which the secondary amine (or salt thereof) is used (either just as it is or in the form of a solution), the type and amount of basic compound that can be used as needed when the secondary amine is a salt, the type and amount of solvent that can be used as needed (although the use of water is not preferred), the reaction temperature, the reaction time (the criteria for setting the reaction time are the conversion of the cyclic hemiacetal and/or the selectivity to the produced aminoether), the reaction apparatus, the order in which the cyclic hemiacetal and secondary amine (or salt thereof) are added (whether they are added all at once, or are added continuously or intermittently), the reaction form (whether batch, semi-batch, or continuous), and so forth.

It may be preferable in terms of promoting the reaction for the production of the aminoether by the reaction between the cyclic hemiacetal of Formula 1 and the secondary amine of Formula 2a to be conducted while the water that is produced is removed. Methods that can be employed for removing the water produced during the reaction include distilling the water off from the system, and physically or chemically absorbing the water with a desiccant. When a method in which the water is distilled off from the system is employed, it is preferable for an organic solvent capable of forming an azeotropic mixture with water, such as benzene, toluene, pentane, cyclohexane, or petroleum ether, to be present in the reaction system, and for the water to be distilled off in the form of an azeotropic mixture with this organic solvent. When a method in which the water is absorbed by a desiccant is employed, the desiccant can be molecular sieves, calcium chloride, magnesium sulfate, sodium sulfate, or another such physical desiccant; calcium hydride, lithium aluminum hydride, or another such chemical desiccant; or the like. When the water is removed from the reaction system in the form of an azeotropic mixture with an organic solvent, the azeotropic mixture thus obtained can be subjected to phase separation, contact with a desiccant, or another such treatment, and the recovered solvent can then be supplied to the reaction system and reused.

Upon completion of the reaction between the cyclic hemiacetal and the secondary amine according to manufacturing method B, the aminoether of Formula 4a, which is the targeted intermediate synthesis product, can be obtained at a high purity by, for example, subjecting the resulting reaction mixture to distillation, crystallization, column chromatography, or another such separation and purification process. A high-purity refined product can be used as the aminoether in the hydrogenation reaction of the aminoether in manufacturing method B, but the reaction mixture obtained from the reaction between the cyclic hemiacetal and the secondary amine may instead be used just as it is, or a crude aminoether obtained by subjecting this reaction mixture to a simple separation process may be used. Unreacted secondary amine can be recovered for reuse.

Any hydrogenation reaction method that can be used in the ordinary hydrogenation of an enamine can also be employed as the hydrogenation reaction of the aminoether of Formula 4a, but a method comprising the reaction of this aminoether with hydrogen in the presence of a hydrogenation catalyst is industrially advantageous. Examples of hydrogenation catalysts that can be used include catalysts whose active component is a metal such as palladium, rhodium, nickel, or platinum. This hydrogenation catalyst can be in the form of the metal itself that serves as the active component; an oxide of this metal; an alloy of this metal with another metal; a carried catalyst in which the metal (or oxide or alloy) that serves as the active component is carried on activated charcoal, alumina, silica gel, diatomaceous earth, or another such carrier; or the like. The amount in which the hydrogenation catalyst is used is not necessarily limited, but is usually between 0.0001 and 0.2 weight part per weight part of the aminoether of Formula 4a. From the standpoints of reaction rate and the cost of manufacturing the targeted aminoalcohol, it is preferable for this amount to be between 0.005 and 0.1 weight part per weight part of the aminoether of Formula 4a.

The use of a solvent is not necessarily required in the hydrogenation reaction of the aminoether, but a solvent may be used, so long as it has no adverse effect on the reaction in question. Solvents that can be used include water; methanol, ethanol, propanol, and other alcohol solvents; diethyl ether, tetrahydrofuran, dioxane, and other ether solvents; and pentane, hexane, cyclohexane, benzene, toluene, xylene, and other hydrocarbon solvents. These can be used singly or in mixtures of two or more types. When a solvent is used, the amount in which it is used is usually between 0.1 and 10 weight parts per weight part of the aminoether of Formula 4a.

In the hydrogenation reaction of the aminoether, hydrogen is brought into contact with a mixture containing the aminoether and the hydrogenation catalyst. Examples of the form of this contact include having hydrogen gas be present in the atmosphere of the reaction system in which this mixture is present, and introducing (bubbling) hydrogen gas into the mixture. The partial pressure of the hydrogen in the reaction system is not necessarily limited, but is usually between 0.5 and 100 atm (absolute pressure). As long as there is no adverse effect on the reaction in question, a gas other than hydrogen (such as nitrogen or argon) may be contained in the gas phase of the reaction system.

The reaction temperature is not necessarily limited in the hydrogenation reaction of the aminoether, but a temperature between 20 and 180° C. is usually employed, and from the standpoints of a high reaction rate and a high selectivity to the targeted aminoalcohol, it is preferable to employ a temperature between 40 and 140° C.

The required reaction time is not necessarily limited in the hydrogenation reaction of the aminoether, and the reaction time (the residence time in the case of a continuous reaction process) can be appropriately set on the basis of the conversion of the aminoether and/or the selectivity to the produced aminoalcohol, as determined by a quantitative analysis means such as gas chromatography. Usually, though, the time is between 0.5 and 20 hours.

A variety of opperations can be employed as desired for conducting the hydrogenation reaction of the aminoether This reaction can be conducted without the use of any special apparatus (such as an autoclave). For example, the reaction can be conducted by batch, semi-batch, or continuous process by using a general-purpose apparatus to mix the aminoether and hydrogenation catalyst by stirring or another such means under a hydrogen gas atmosphere and under the required temperature and hydrogen pressure.

Upon completion of the hydrogenation reaction of the aminoether, the aminoalcohol of Formula 3a that is the targeted substance can be obtained at a high purity by, for example, removing the hydrogenation catalyst from the obtained reaction mixture by filtration, centrifugation, or the like, and then subjecting the resulting mixture to distillation, crystallization, column chromatography, or another such separation and purification process. Unreacted secondary amine can be recovered for reuse.

Further, an aminoalcohol expressed by the Formula 3a'

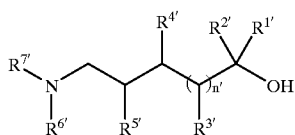

(3a')

(where n' is 0 or 1; $R^{1'}$ and $R^{2'}$ are each a hydrogen atom, a monovalent saturated hydrocarbon group which is optionally substituted, or a monovalent aromatic group which is optionally substituted, or $R^{1'}$ and $R^{2'}$ are bonded together into a divalent saturated hydrocarbon group which is optionally substituted; $R^{3'}$ and $R^{5'}$ are each a hydrogen atom, a monovalent saturated hydrocarbon group which is optionally substituted, or a monovalent aromatic group which is optionally substituted; $R^{4'}$ is a monovalent saturated hydrocarbon group which is optionally substituted or a monovalent aromatic group which is optionally substituted; when n is 0, $R^{6'}$ and $R^{7'}$ are each a monovalent saturated hydrocarbon group which is optionally substituted or a monovalent aromatic group which is optionally substituted, and when n is 1, $R^{6'}$ is a monovalent saturated hydrocarbon group having one carbon atom or greater which group is optionally substituted or a monovalent aromatic group which is optionally substituted, and $R^{7'}$ is a monovalent saturated hydrocarbon group having two carbon atoms or greater which group is optionally substituted or a monovalent aromatic group which is optionally substituted, or $R^{6'}$ and $R^{7'}$ are bonded together into a divalent saturated aliphatic group which is optionally substituted) is a novel compound which can be manufactured in the same manner as the aminoalcohol of Formula 3, and is also encompassed by the present invention.

An aminoether expressed by Formula 4a

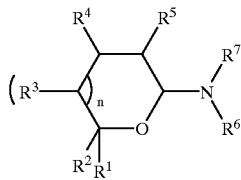

(4a)

(where n is 0 or 1; $R^1$ and $R^2$ are each a hydrogen atom, a monovalent saturated hydrocarbon group which is optionally substituted, or a monovalent aromatic group which is optionally substituted, or $R^1$ and $R^2$ are bonded together into a divalent saturated hydrocarbon group which is optionally substituted; $R^3$, $R^4$, and $R^5$ are each a hydrogen atom, a monovalent saturated hydrocarbon group which is optionally substituted, or a monovalent aromatic group which is optionally substituted; and $R^6$ and $R^7$ are each a monovalent saturated hydrocarbon group which is optionally substituted or a monovalent aromatic group which is optionally substituted, or $R^6$ and $R^7$ are bonded together into a divalent saturated aliphatic group which is optionally substituted) is also a novel compound which is a precursor of the aminoalcohol obtained by manufacturing method B, and is encompassed by the present invention.

The aminoalcohol of Formula 3a obtained by manufacturing methods A and B of the present invention is an aminoalcohol classified as a tertiary amine, in which one of the three substituents bonded to the nitrogen atom of the amino group is an organic group having a carbon-skeleton main chain which has four or five carbon atoms and links a hydroxyl group to the nitrogen atom of the amino group. Because of its chemical structure, this aminoalcohol can be used in a wide range of applications as a fiber auxiliary, an emulsifier, a plasticizer, a gas absorbent, a rustproofing agent, a cosmetic raw material, a synthetic deteorrgent, a shoe polish, a glazing agent, a wax, a surfactant, an additive for cutting oil, an additive for lubricating oil, a pesticide additive, an organic solvent, a pH regulator, a neutralizer, an urethanation catalyst, or the like. Also, if the hydroxyl group is acrylated or methacrylated, this aminoalcohol will be useful as a raw material for acrylic resins, thermoplastic elastomers, resin modifiers, pressure-sensitive adhesives, ion exchange resins, fiber treatment agents, UV-curing inks, paints, and adhesives, electron beam-curing inks, paints, and adhesives, radiation-curing inks, paints, and adhesives, and so forth.

Next, manufacturing methods C and D of the present invention will be described.

The above-mentioned manufacturing methods C and D of the present invention are similar in that they both make use of the cyclic hemiacetal of Formula 1 and the primary amine of Formula 2b as the main raw materials, and the target substance is the aminoalcohol of Formula 3b, which is classified as a tertiary amine.

In Formula 2b, which represents the primary amine that is one of the raw materials, $R^8$ is a monovalent saturated hydrocarbon group which is optionally substituted or a monovalent aromatic group which is optionally substituted, and includes the same as those exemplified for R in Formula 2a.

Specific examples of the primary amine of Formula 2b include methylamine, ethylamine, isopropylamine, propylamine, isobutylamine, butylamine, t-butylamine, octylamine, (2-ethylhexyl)amine, cyclohexylamine, N-(3-aminopropyl)morpholine, aniline, o-toluidine, m-toluidine, p-toluidine, p-phenetidine, mesidine, 4-amino-3-methyl-N, N-diethylaniline, 2-aminopyridine, 3-aminopyridine, 4-aminopyridine, α-naphthylamine, benzylamine, phenethylamine, ethanolamine, N,N-dimethylethylenediamine, 3-(dimethylamino)propylamine, and 3-methoxypropylamine.

The primary amine of Formula 2b used in the reaction according to manufacturing methods C and D may be in the form of a salt. Examples of salts that can be used include salts formed from a primary amine and hydrochloric acid, sulfuric acid, nitric acid, acetic acid propionic acid, or another such protic acid. Typical examples of such salts include methylammonium chloride, di(methylammonium) sulfate, methylammonium nitrate, methylammonium acetate, and methylammonium propionate.

First, of the manufacturing methods of the present invention, manufacturing method C will be described.

The proportions in which the cyclic hemiacetal of Formula 1 and the primary amine of Formula 2b (or salt thereof) are used in manufacturing method C are not necessarily limited, but stoichiometrically, 2 moles of cyclic hemiacetal is reacted with 1 mole of primary amine, so the cyclic hemiacetal is preferably used in an amount of 1.8 to 10 moles, and even more preferably 2.0 to 4.0 moles, per mole of primary amine.

In supplying the primary amine of Formula 2b (or a salt thereof) to the reaction system in the reaction according to manufacturing method C, the form of the primary amine is not necessarily limited, and the primary amine may be supplied just as it is, or it may first be diluted with a solvent. Specific examples of solvents for diluting the primary amine include water, methanol, ethanol, propanol, diethyl ether, tetrahydrofuran, dioxane, pentane, hexane, cyclohexane, benzene, toluene, and xylene. These solvents can be used singly or in mixtures of two or more types. When a salt of a primary amine and a protic acid is used as the primary amine, better results may be obtained if a basic compound is present in the reaction system. Specific examples of this basic compound include lithium hydroxide, sodium hydroxide, potassium hydroxide, lithium acetate, sodium acetate, potassium acetate, triethylamine, tributylamine, trioctylamine, and pyridine. When this basic compound is used, the amount in which it is used is usually no more than 10 moles, and preferably no more than 2 moles, per mole of the salt of a primary amine.

The reaction in manufacturing method C involves reacting the cyclic hemiacetal of Formula 1 with the primary amine of Formula 2b and hydrogen in the presence of a hydrogenation catalyst. Any catalyst that is generally used in catalytic hydrogenation reactions can be used as this hydrogenation catalyst, examples of which include catalysts whose active component is a metal such as palladium, rhodium, nickel, or platinum. This hydrogenation catalyst can be in the form of the metal itself that serves as the active component; an oxide of this metal; an alloy of this metal with another metal; a carried catalyst in which the metal (or oxide or alloy) that serves as the active component is carried on activated charcoal, alumina, silica gel, diatomaceous earth, or another such carrier; or the like. The amount in which the hydrogenation catalyst is used is not necessarily limited, but is usually between 0.0001 and 0.2 weight part per weight part of the cyclic hemiacetal of Formula 1. From the standpoints of reaction rate and the cost of manufacturing the targeted aminoalcohol, it is preferable for this amount to be between 0.005 and 0.1 weight part per weight part of the cyclic hemiacetal of Formula 1.

The use of a solvent is not necessarily required in the reaction of manufacturing method c, but a solvent may be used, so long as it has no adverse effect on the reaction in question. Solvents that can be used include water; methanol, ethanol, propanol, and other alcohol solvents; diethyl ether, tetrahydrofuran, dioxane, and other ether solvents; and pentane, hexane, cyclohexane, benzene, toluene, xylene, and other hydrocarbon solvents. These can be used singly or in mixtures of two or more types. When a solvent is used, the amount in which it is used is usually between 0.1 and 10 weight parts per weight part of the cyclic hemiacetal of Formula 1.

In the reaction in manufacturing method C, hydrogen is brought into contact with a mixture containing the cyclic hemiacetal of Formula 1, the primary amine of Formula 2b, and the hydrogenation catalyst. Examples of the form of this contact include having hydrogen gas be present in the atmosphere of the reaction system in which this mixture is present, and introducing (bubbling) hydrogen gas into the mixture. The partial pressure of the hydrogen in the reaction system is not necessarily limited, but is usually between 0.5 and 100 atm (absolute pressure). As long as there is no adverse effect on the reaction in question, a gas other than hydrogen (such as nitrogen or argon) may be contained in the gas phase of the reaction system.

The reaction temperature is not necessarily limited in the reaction of manufacturing method C, but a temperature between 20 and 180° C. is usually employed, and from the standpoints of a high reaction rate and a high selectivity to the targeted aminoalcohol, it is preferable to employ a temperature between 40 and 140° C.

The required reaction time is not necessarily limited in the reaction of manufacturing method C, and the reaction time (the residence time in the case of a continuous reaction process) can be appropriately set on the basis of the conversion of the primary amine and/or the selectivity to the produced aminoalcohol, as determined by a quantitative analysis means such as gas chromatography. Usually, though, the time is between 0.5 and 20 hours.

A variety of operations can be employed as desired for conducting the reaction of manufacturing method C. This reaction can be conducted without the use of any special apparatus (such as an autoclave). For example, the reaction can be conducted by batch, semi-batch, or continuous process by using a general-purpose apparatus to mix the cyclic hemiacetal of Formula 1, the primary amine of Formula 2b (or a salt thereof), and the hydrogenation catalyst by stirring or another such means under a hydrogen gas atmosphere and under the required temperature and hydrogen pressure. There are no particular restrictions on the order or rate at which the various components are mixed in the reaction, and the reaction may be commenced after all of the liquid or solid components supplied to the reaction (namely, the cyclic hemiacetal, primary amine, and hydrogenation catalyst) have been mixed at once, or the reaction may be conducted while either the cyclic hemiacetal or the primary amine is added to the reactor wherein the other component has been supplied along with the hydrogenation catalyst. In the latter case, part of components can be added during the reaction in a variety of forms, such as continuous addition, or intermittent addition that is divided up into a plurality of batches.

When conditions are employed such that the added amount of the cyclic hemiacetal of Formula 1 is less than 2 moles per mole of the primary amine of Formula. 2b over a sufficiently long time during the reaction, side reactions such as those brought about by self-condensation of the cyclic hemiacetals can be suppressed, allowing the yield and selectivity of the targeted aminoalcohol of Formula 3b to be higher. In this respect, a semi-batch reaction process comprising conducting the reaction while adding the cyclic hemiacetal to a mixture of the primary amine and the hydrogenation catalyst, a continuous reaction process comprising conducting the reaction while the cyclic hemiacetal, primary amine, and hydrogenation catalyst are continuously supplied to the reaction system and part of the reaction mixture is continuously taken out from the reaction system, or the like is preferred.

Upon completion of the reaction of manufacturing method C, the aminoalcohol of Formula 3b that is the targeted substance can be obtained at a high purity by, for example, removing the hydrogenation catalyst from the obtained reaction mixture by filtration, centrifugation, or the like, and then subjecting the resulting mixture to distillation, crystallization, column chromatography, or another such separation and purification process. Unreacted primary amine can be recovered for reuse.

Next, of the manufacturing methods of the present invention, manufacturing method D will be described.

Manufacturing method D includes a step of reacting the cyclic hemiacetal of Formula 1 and the primary amine of Formula 2b, and a step of manufacturing the aminoalcohol of Formula 3b by the hydrogenation of the reaction mixture obtained in the former reaction step.

Except for the fact that there is no need for hydrogen or a hydrogenation catalyst, the reaction between the cyclic hemiacetal of Formula 1 and the primary amine of Formula 2b according to manufacturing method D can be conducted in substantially the same manner as the reaction of the cyclic hemiacetal of Formula 1 with the primary amine of Formula 2b and hydrogen in the presence of a hydrogenation catalyst according to manufacturing method C. Specifically, the two reactions share the same conditions for the proportions in which the cyclic hemiacetal and primary amine (or salt thereof) are used, the form in which the primary amine (or salt thereof) is used (either just as it is or in the form of a solution), the type and amount of basic compound that can be used as needed when the primary amine is a salt, the type and amount of solvent that can be used as needed (although the use of water is not preferred), the reaction temperature, the reaction time (the criteria for setting the reaction time are the conversion of the primary amine), the reaction apparatus, the order in which the cyclic hemiacetal and primary amine (or salt thereof) are added (whether they are added all at once, or are added continuously or intermittently), the reaction form (whether batch, semi-batch, or continuous), and so forth.

It may be preferable in terms of promoting the reaction for the reaction between the cyclic hemiacetal of Formula 1 and the primary amine of Formula 2b to be conducted while the water that is produced is removed to outside the system. Methods that can be employed for removing the water produced during the reaction include distilling the water off from the system, and physically or chemically absorbing the water with a desiccant. When a method in which the water is distilled off from the system is employed, it is preferable for an organic solvent capable of forming an azeotropic mixture with water, such as benzene, toluene, pentane, cyclohexane, or petroleum ether, to be present in the reaction system, and for the water to be distilled off in the form of an azeotropic mixture with this organic solvent. When a method in which the water is absorbed by a desiccant is employed, the desiccant can be molecular sieves, calcium chloride, magnesium sulfate, sodium sulfate, or another such physical desiccant; calcium hydride, lithium aluminum hydride, or another such chemical desiccant; or the like. When the water is removed from the reaction system in the form of an azeotropic mixture with an organic solvent, the azeotropic mixture thus obtained can be subjected to phase separation, contact with a desiccant, or another such treatment, and the recovered solvent can then be supplied to the reaction system and reused.

It is surmised that a compound of Formula 6

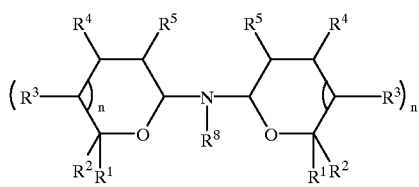

(6)

(where n, $R^1$, $R^2$, $R^3$, $R^4$, $R^5$ and $R^8$ are defined the same as above), which is a condensation reaction product of two molecules of the cyclic hemiacetal of Formula 1 with one molecule of the primary amine of Formula 2b, is present in the reaction mixture obtained by the reaction between the cyclic hemiacetal of Formula 1 and the primary amine of Formula 2b according to manufacturing method D. However, because the stability of this condensation reaction product is low, the above-mentioned reaction mixture is preferably supplied to the subsequent hydrogenation process either directly as it is or after being subjected to only a simple treatment such as concentration by evaporating off the low-boiling materials, without the condensation reaction product being isolated first.

Any hydrogenation reaction method that can be used in the ordinary hydrogenation of an enamine can also be employed as the hydrogenation reaction of the reaction mixture obtained by the reaction between the cyclic hemiacetal of Formula 1 and the primary amine of Formula 2b, but a method in which this reaction mixture brought into contact with hydrogen in the presence of a hydrogenation catalyst is industrially advantageous. Examples of hydrogenation catalysts that can be used include catalysts whose active component is a metal such as palladium, rhodium, nickel, or platinum. This hydrogenation catalyst can be in the form of the metal itself that serves as the active component; an oxide of this metal; an alloy of this metal with another metal; a carried catalyst in which the metal (or oxide or alloy) that serves as the active component is carried on activated charcoal, alumina, silica gel, diatomaceous earth, or another such carrier; or the like. The amount in which the hydrogenation catalyst is used is not necessarily limited, but is usually an amount of 0.01 to 20 wt % with respect to the weight of that portion of the reaction mixture obtained by the reaction between the cyclic hemiacetal and the primary amine (may be a mixture that has undergone a simple treatment after the reaction) which is supplied to the hydrogenation process. From the standpoints of reaction rate and the cost of manufacturing the targeted aminoalcohol, it is preferable for this amount to be between 0.5 and 10 wt %.

The use of a solvent is not necessarily required in the hydrogenation reaction of manufacturing method D, but a solvent may be used, so long as it has no adverse effect on the reaction in question. Solvents that can be used include water; methanol, ethanol, propanol, and other alcohol solvents; diethyl ether, tetrahydrofuran, dioxane, and other ether solvents; and pentane, hexane, cyclohexane, benzene, toluene, xylene, and other hydrocarbon solvents. These can be used singly or in mixtures of two or more types. When a solvent is used, the amount in which it is used is usually no more than 10 times the weight in which the reaction mixture obtained by the reaction between the cyclic hemiacetal and the primary amine (may be a mixture that has undergone a simple treatment after the reaction) is supplied to the hydrogenation reaction process.

In the hydrogenation reaction in manufacturing method D, hydrogen is brought into contact with a mixture containing the reaction mixture obtained by the reaction between the cyclic hemiacetal of Formula 1 and the primary amine of Formula 2b, and the hydrogenation catalyst (hereinafter the former mixture will be referred to as the "mixture for hydrogenation"). Examples of the form of this contact include having hydrogen gas be present in the atmosphere of the reaction system in which the mixture for hydrogenation is present, and introducing (bubbling) hydrogen gas into the mixture for hydrogenation. The partial pressure of the hydrogen in the reaction system is not necessarily limited, but is usually between 0.5 and 100 atm (absolute pressure). As long as there is no adverse effect on the reaction in question, a gas other than hydrogen (such as nitrogen or argon) may be contained in the gas phase of the reaction system.

The reaction temperature is not necessarily limited in the reaction of manufacturing method D, but a temperature between 20 and 180° C. is usually employed, and from the standpoints of a high reaction rate and a high selectivity to the targeted aminoalcohol of Formula 3b, it is preferable to employ a temperature between 40 and 140° C.

The required reaction time is not necessarily limited in the hydrogenation reaction of manufacturing method D, and the reaction time (the residence time in the case of a continuous reaction process) can be appropriately set on the basis of the selectivity to the aminoalcohol of Formula 3b, as determined by a quantitative analysis means such as gas chromatography. Usually, though, the time is between 0.5 and 20 hours.

A variety of opperations can be employed as desired for conducting the hydrogenation reaction of manufacturing method D. This reaction can be conducted without the use of any special apparatus (such as an autoclave). For example, the reaction can be conducted by batch, semi-batch, or continuous process by using a general-purpose apparatus to mix the reaction mixture obtained by the reaction between the cyclic hemiacetal of Formula 1 and the primary amine of Formula 2b with the hydrogenation catalyst by stirring or another such means under a hydrogen gas atmosphere and under the required temperature and hydrogen pressure.

Upon completion of the hydrogenation reaction in manufacturing method D, the aminoalcohol of Formula 3b that is the targeted substance can be obtained at a high purity by, for example, removing the hydrogenation catalyst from the obtained reaction mixture by filtration, centrifugation, or the like, and then subjecting the resulting mixture to distillation, crystallization, column chromatography, or another such separation and purification process. Unreacted primary amine can be recovered for reuse.

The aminoalcohol of Formula 3b obtained by manufacturing methods C and D of the present invention is an aminoalcohol classified as a tertiary amine, in which two or more of the three substituents bonded to the nitrogen atom of the amino group are organic groups (such as alkylene groups) having a carbon-skeleton main chain with four or five carbon atoms and which link hydroxyl group to the nitrogen atom of the amino group. Because of its chemical structure, this aminoalcohol can be used as a fiber auxiliary, an emulsifier, a plasticizer, a gas absorbent, a rustproofing agent, a cosmetic raw material, a synthetic detergent, a shoe polish, a glazing agent, a wax, a surfactant, an additive for cutting oil, an additive for lubricating oil, a pesticide additive, an organic solvent, a pH regulator, a neutralizer, an urethanation catalyst, or the like. Also, if the hydroxyl groups are acrylated or methacrylated, this aminoalcohol will be useful as a raw material for acrylic resins, thermoplastic elastomers, resin modifiers, pressure-sensitive adhesives, ion exchange resins, fiber treatment agents, UV-curing inks, paints, and adhesives, electron beam-curing inks, paints, and adhesives, radiation-curing inks, paints, and adhesives, and so forth.

Next, manufacturing methods E and F of the present invention will be described.

Manufacturing method E is a method for manufacturing the aminoalcohol of Formula 3c in one reaction step from the cyclic hemiacetal of Formula 1 by simultaneously reacting the cyclic hemiacetal of Formula 1, the nitrogen-containing compound of Formula 2c, and hydrogen in the presence of a hydrogenation catalyst. Manufacturing method F is a method for manufacturing the aminoalcohol of Formula 3c in two reaction steps from the cyclic hemiacetal of Formula 1 by first reacting the cyclic hemiacetal of Formula 1 with the nitrogen-containing compound of Formula 2c, and then subjecting the reaction mixture thus obtained to reaction with hydrogen in the presence of a hydrogenation catalyst.

Specifically, a typical example of the cyclic hemiacetal of Formula 1 which is one of the raw materials is a cyclic hemiacetal expressed by Formula 1'

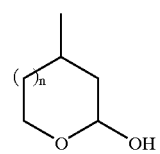

(1')

(where n is 0 or 1),
including 2-hydroxy-4-methyltetrahydropyran (when n=1) or 2-hydroxy-4-methyltetrahydrofuran (when n=0).

In case of using the cyclic hemiacetal of Formula 1' as the cyclic hemiacetal of Formula 1, manufacturing method E includes a method for manufacturing the aminoalcohol expressed by Formula (3c')

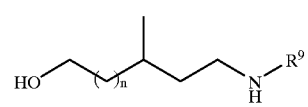

(3c')

(where n and $R^9$ are defined as above), which method comprises:

reacting the cyclic hemiacetal of Formula 1' with the nitrogen-containing compound of Formula 2c and hydrogen in the presence of a hydrogenation catalyst to obtain the aminoalcohol of Formula 3c'; and manufacturing method F includes a method for manufacturing the aminoalcohol expressed by Formula 3c', which method comprises:

reacting the cyclic hemiacetal of Formula 1' with the nitrogen-containing compound of Formula 2c; and subjecting the reaction mixture thus obtained to reaction with hydrogen in the presence of a hydrogenation catalyst to obtain the aminoalcohol of Formula 3c'.

The cyclic hemiacetal of Formula 1' can be synthesized by a known method, but of these, a method for synthesizing a cyclic hemiacetal by subjecting an alkenol compound expressed by the following Formula 5' to a hydroformylation reaction is preferable because the product can be manufactured inexpensively on an industrial scale.

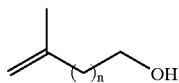

(5')

(where formula, n is 1 or 0)

An alkenol compound when n is 1 in Formula 5' is 2-methyl-buten-4-ol, and an alkenol compound when n is 0 is 2-methyl-1-propen-3-ol.

A variety of known reaction methods can be employed for the hydroformylation of the alkenol compound of Formula 5', but a method in which the alkenol compound of Formula 5' is reacted with carbon monoxide and hydrogen in the presence of a rhodium compound and a tertiary organophosphorus compound can be used to particular advantage. For instance, Japanese Patent Application Laid-Open No. S60-19781, U.S. Pat. No. 4,663,468, U.S. Pat. No. 4,808,737 and so forth discuss a method for the hydroformylation of 2-methyl-1-buten-4-ol, and Japanese Patent Application Laid-Open No. H3-261776 and U.S. Pat. No. 5,684,167 discuss a method for the hydroformylation of 2-methyl-1-propen-3-ol.

When a cyclic hemiacetal obtained by the hydroformylation of the alkenol compound of Formula 5' is used as a raw material in manufacturing method E or F, a refined cyclic hemiacetal obtained by subjecting the reaction mixture obtained by hydroformylation to distillation, recrystallization, or other such separation and refinement can be used, but the hydroformylation reaction mixture containing the cyclic hemiacetal, rhodium compound, tertiary organophosphorus compound, by-products, and so on may instead be used just as it is, or a crude cyclic hemiacetal obtained by subjecting this reaction mixture to a simple separation process may be used.

The nitrogen-containing compound of Formula 2c, which is another of the raw materials, encompasses ammonia (when $R^9$ is a hydrogen atom) and primary amines (when $R^9$ is a monovalent saturated hydrocarbon group which is optionally substituted or a monovalent aromatic group which is optionally substituted).

When the nitrogen-containing compound of Formula 2c is ammonia, either liquid ammonia or aqueous ammonia can be used. Ammonia can be used in a salt form thereof. Examples of such salts that can be used include salts formed from ammonia and a protic acid such as hydrochloric acid, sulfuric acid, nitric acid, acetic acid, propionic acid. A typical example of such a salt includes ammonium chloride, diammonium sulufate, ammonium nitrate, ammonium acetate, ammonium propionate and the like.

When the nitrogen-containing compound of Formula 2c is a primary amine, $R^9$ in Formula 2c is defined similarly to $R^8$ in the primary amine of Formula 2b and examples thereof include the same as those exemplified for $R^6$ of Formula 2a. Therefore, specific examples of the nitrogen-containing compound being a primary amine are the same as those listed for the primary amine of Formula 2b.

Manufacturing method E of the present invention, as mentioned above, is a method for manufacturing the aminoalcohol of Formula 3c in one reaction step from the cyclic hemiacetal of Formula 1 by simultaneously reacting the cyclic hemiacetal of Formula 1, the nitrogen-containing compound of Formula 2c (namely, ammonia or a primary amine), and hydrogen in the presence of a hydrogenation catalyst.

In manufacturing method E, the proportion in which the nitrogen-containing compound of Formula 2c is used with respect to the cyclic hemiacetal of Formula 1 is not necessarily limited. However, because this cyclic hemiacetal is an equivalent of an aldehyde, in its reaction with the nitrogen-containing compound of Formula 2c and hydrogen, there is the possibility that it will be hydrogenated without reacting with the nitrogen-containing compound of Formula 2c, and the possibility that it will undergo self-condensation, so there is the danger that costs will be driven up during manufacture. Therefore, when suppressing unintended hydrogenation or self-condensation and the volumetric efficiency of the reactor are taken into account, the amount in which the nitrogen-containing compound of Formula 2c is used should be between 0.9 and 50 moles, and preferably between 1 and 20 moles, per mole of cyclic hemiacetal of Formula 1 used.

The form of the ammonia is not necessarily limited in the supply of this ammonia (or a salt thereof) to the reaction system, and ammonia may be supplied just as it is or after being diluted with a solvent. Specific examples of solvents for diluting the ammonia include water, methanol, ethanol, propanol, diethyl ether, tetrahydrofuran, dioxane, pentane, hexane, cyclohexane, benzene, toluene, and xylene. These solvents can be used singly or in mixtures of two or more types.

Nor is the form of the primary amine necessarily limited in the supply of this primary amine (or a salt thereof) to the reaction system, and the primary amine may be supplied just as it is or after being diluted with a solvent. Specific examples of solvents for diluting the primary amine include water, methanol, ethanol, propanol, diethyl ether, tetrahydrofuran, dioxane, pentane, hexane, cyclohexane, benzene, toluene, and xylene. These solvents can be used singly or in mixtures of two or more types.

When a salt formed from ammonia or a primary amine and a protic acid is used as the ammonia or the primary amine, better results may be obtained if a basic compound is present in the reaction system. Specific examples of this basic compound include lithium hydroxide, sodium hydroxide, potassium hydroxide, lithium acetate, sodium acetate, potassium acetate, triethylamine, tributylamine, trioctylamine, and pyridine. When this basic compound is used, the amount in which it is used is usually no more than 10 moles, and preferably no more than 2 moles, per mole of the salt of ammonia or a primary amine.

Any catalyst that is generally used in catalytic hydrogenation reactions can be used as the hydrogenation catalyst used in manufacturing method E, examples of which include catalysts whose active component is a metal such as palladium, rhodium, nickel, or platinum.

This hydrogenation catalyst can be in the form of the metal itself that serves as the active component; an oxide of this metal; an alloy of this metal with another metal; a carried catalyst in which the metal (or oxide or alloy) that serves as the active component is carried on activated charcoal, alumina, silica gel, diatomaceous earth, or another such carrier; or the like. The amount in which the hydrogenation catalyst is used is not necessarily limited, but is usually between 0.0001 and 0.2 weight part per weight part of the cyclic hemiacetal of Formula 1. From the standpoints of reaction rate and the cost of manufacturing the targeted aminoalcohol, it is preferable for this amount to be between 0.005 and 0.1 weight part.

The use of a solvent is not necessarily required, but a solvent may be used, so long as it has no adverse effect on the reaction in question. Solvents that can be used include water; methanol, ethanol, propanol, 1-butenol, 1-octanol and other alcohol solvents; diethyl ether, tetrahydrofuran, dioxane, and other ether solvents; and pentane, hexane, cyclohexane, benzene, toluene, xylene, and other hydrocarbon solvents. These can be used singly or in mixtures of two or more types. When a solvent is used, the amount in which it is used is usually between 0.1 and 10 weight parts per weight part of the cyclic hemiacetal of Formula 1.

Examples of the form in which hydrogen is brought into contact with the mixture containing the cyclic hemiacetal of Formula 1, the nitrogen-containing compound of Formula 2c, and the hydrogenation catalyst include having hydrogen gas be present in the atmosphere of the reaction system in which this mixture is present, and introducing (bubbling) hydrogen gas into the mixture. The partial pressure of the hydrogen in the reaction system is not necessarily limited, but is usually between 0.5 and 150 atm (absolute pressure). As long as there is no adverse effect on the reaction in question, a gas other than hydrogen (such as nitrogen or argon) may be contained in the gas phase of the reaction system.

The reaction temperature is not necessarily limited, but a temperature between 20 and 180° C. is usually employed, and from the standpoints of a high reaction rate and a high selectivity to the targeted aminoalcohol, it is preferable to employ a temperature between 40 and 140° C.

The required reaction time is not necessarily limited, and the reaction time (the residence time in the case of a continuous reaction process) can be appropriately set on the basis of the conversion of the cyclic hemiacetal and/or the selectivity to the produced aminoalcohol, as determined by a quantitative analysis means such as gas chromatography. Usually, though, the time is between 0.5 and 20 hours.

A variety of operations can be employed as desired for conducting the reaction. This reaction can be conducted without the use of any special apparatus (such as an autoclave). For example, the reaction can be conducted by batch, semi-batch, or continuous process by using a general-purpose apparatus to mix the cyclic hemiacetal of Formula 1, the nitrogen-containing compound of Formula 2c, and the hydrogenation catalyst by stirring or another such means under a hydrogen gas atmosphere and under the required temperature and hydrogen pressure. There are no particular restrictions on the order or rate at which the various components are mixed in the reaction, and the reaction may be commenced after all of the liquid or solid components supplied to the reaction (namely, the cyclic hemiacetal, nitrogen-containing compound, and hydrogenation catalyst) have been mixed at once, or the reaction may be conducted while either the cyclic hemiacetal or the nitrogen-containing compound is added to the reactor wherein the other component has been supplied along with the hydrogenation catalyst. In the latter case, part of components can be added during the reaction in a variety of forms, such as continuous addition, or intermittent addition that is divided up into a plurality of batches.

When a means is chosen such that the nitrogen-containing compound of Formula 2c will be present in the reaction system in a proportion that is a large excess with respect to the cyclic hemiacetal of Formula 1 over most of the time during the reaction, side reactions such as those brought about by self-condensation of the cyclic hemiacetals of Formula 1 can be suppressed, allowing the yield and selectivity of the targeted aminoalcohol to be higher. In this respect, a semi-batch reaction process comprising conducting the reaction while adding the cyclic to a mixture of the nitrogen-containing compound of Formula 2c and the hydrogenation catalyst, a continuous reaction process comprising conducting the reaction while the cyclic hemiacetal of Formula 1, the nitrogen-containing compound of Formula 2c, and hydrogenation catalyst are continuously supplied to the reaction system and part of the reaction mixture is continuously taken out from the reaction system, or the like is preferred.

Upon completion of the reaction, the aminoalcohol of Formula 3c that is the targeted substance can be obtained at a high purity by, for example, removing the hydrogenation catalyst from the obtained reaction mixture by filtration, centrifugation, or the like, and then subjecting the resulting mixture to distillation, crystallization, column chromatography, or another such separation and purification process. Unreacted nitrogen-containing compound can be recovered for reuse.

Next, manufacturing method F will be described.

As mentioned above, manufacturing method F is a method for manufacturing the aminoalcohol of Formula 3c in two reaction steps from the cyclic hemiacetal of Formula 1 by first reacting the cyclic hemiacetal of Formula 1 with the nitrogen-containing compound of Formula 2c, and then subjecting the reaction mixture thus obtained to reaction with hydrogen in the presence of a hydrogenation catalyst. Here, it is considered that when the cyclic hemiacetal of Formula 1 is reacted with the nitrogen-containing compound of Formula 2c, the aminoether of the following Formula 4b is produced when at least this nitrogen-containing compound is a primary amine (when $R^9$ is a monovalent saturated hydrocarbon group which is optionally substituted or a monovalent aromatic group which is optionally substituted.

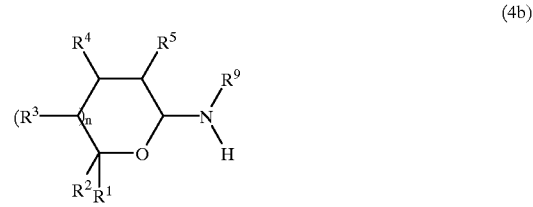

(4b)

(where n, $R^1$, $R^2$, $R^3$, $R^4$, $R^5$ and $R^9$ are defined the same as above)

Except for the fact that there is no need for hydrogen or a hydrogenation catalyst, the reaction between the cyclic hemiacetal of Formula 1 and the nitrogen-containing compound of Formula 2c in manufacturing method F can be conducted in substantially the same manner as the reaction of the cyclic hemiacetal of Formula 1 with the nitrogen-containing compound of Formula 2c and hydrogen in the presence of a hydrogenation catalyst according to manufacturing method E. Specifically, manufacturing methods E and F share the same conditions for the proportions in which the cyclic hemiacetal of Formula 1 and nitrogen-containing compound of Formula 2c are used, the form in which the nitrogen-containing compound of Formula 2c is used (just as it is, in the form of a salt, in the form of a solution, etc.), the type and amount of basic compound that can be used as needed when the nitrogen-containing compound of Formula 2c is in the form of a salt of ammonia or a primary amine, the type and amount of solvent that can be used as needed, the reaction temperature, the reaction time (the criterion for setting the reaction time is the conversion of the cyclic hemiacetal of Formula 1), the reaction apparatus, the order in which the cyclic hemiacetal and nitrogen-containing compound are added (whether they are added all at once, or are added continuously or intermittently), the reaction form (whether batch, semi-batch, or continuous), and so forth.

When the cyclic hemiacetal of Formula 1 and the nitrogen-containing compound of Formula 2c are reacted, it may be preferable in terms of promoting the reaction for the reaction to be conducted while the water that is produced is removed. Methods that can be employed for removing the water produced during the reaction include distilling the water off from the system, and physically or chemically absorbing the water with a desiccant. When a method in which the water is distilled off from the system is employed, it is preferable for an organic solvent capable of forming an azeotropic mixture with water, such as benzene, toluene, pentane, cyclohexane, or petroleum ether, to be present in the reaction system, and for the water to be distilled off in the form of an azeotropic mixture with this organic solvent. When a method in which the water is absorbed by a desiccant is employed, the desiccant can be molecular sieves, calcium chloride, magnesium sulfate, sodium sulfate, or another such physical desiccant; calcium hydride, lithium aluminum hydride, or another such chemical desiccant; or the like. When the water is removed from the reaction system in the form of an azeotropic mixture with an organic solvent, the azeotropic mixture thus obtained can be subjected to phase separation, contact with a desiccant, or another such treatment, and the recovered solvent can then be supplied to the reaction system and reused.

Upon completion of the reaction between the cyclic hemiacetal of Formula 1 and the nitrogen-containing compound of Formula 2c in manufacturing method F, it may be possible to isolate the reaction product by subjecting the obtained reaction mixture to distillation, crystallization, column chromatography, or another such separation and purification process, but because the stability is low, the reaction mixture is preferably supplied to the hydrogenation reaction either directly as it is or after being subjected to only a simple treatment such as concentration. Unreacted nitrogen-containing compound can be recovered for reuse.

Any hydrogenation reaction method that can be used in the ordinary hydrogenation of an enamine can also be employed as the hydrogenation reaction of the above-mentioned reaction mixture in manufacturing method F, but a method comprising the reaction of this reaction mixture with hydrogen in the presence of a hydrogenation catalyst is industrially advantageous. Examples of hydrogenation catalysts that can be used include catalysts whose active component is a metal such as palladium, rhodium, nickel, or platinum. This hydrogenation catalyst can be in the form of the metal itself that serves as the active component; an oxide of this metal; an alloy of this metal with another metal; a carried catalyst in which the metal (or oxide or alloy) that serves as the active component is carried on activated charcoal, alumina, silica gel, diatomaceous earth, or another such carrier; or the like. The amount in which the hydrogenation catalyst is used is not necessarily limited, but is usually between 0.0001 and 0.2 weight part per weight part of the cyclic hemiacetal of Formula 1 that is the starting substance. From the standpoints of reaction rate and the cost of manufacturing the targeted aminoalcohol, it is preferable for this amount to be between 0.005 and 0.1 weight part.

The use of a solvent is not necessarily required in the hydrogenation reaction in manufacturing method F, but a solvent may be used, so long as it has no adverse effect on the reaction in question. Solvents that can be used include water; methanol, ethanol, propanol, 1-butanol, 1-octanol, and other alcohol solvents; diethyl ether, tetrahydrofuran, dioxane, and other ether solvents; and pentane, hexane, cyclohexane, benzene, toluene, xylene, and other hydrocarbon solvents. These can be used singly or in mixtures of two or more types. When a solvent is used, the amount in which it is used is usually between 0.1 and 10 weight parts per weight part of the starting substance cyclic hemiacetal of Formula 1.

In the hydrogenation reaction in manufacturing method F, hydrogen is brought into contact with a reaction mixture containing the hydrogenation catalyst. Examples of the form of this contact include having hydrogen gas be present in the atmosphere of the reaction system in which this mixture is present, and introducing (bubbling) hydrogen gas into the mixture. The partial pressure of the hydrogen in the reaction system is not necessarily limited, but is usually between 0.5 and 100 atm (absolute pressure). As long as there is no adverse effect on the reaction in question, a gas other than hydrogen (such as nitrogen or argon) may be contained in the gas phase of the reaction system.

The reaction temperature is not necessarily limited in the hydrogenation reaction in manufacturing method F, but a temperature between 20 and 180° C. is usually employed, and from the standpoints of a high reaction rate and a high selectivity to the targeted aminoalcohol, it is preferable to employ a temperature between 40 and 140° C.

The required reaction time is not necessarily limited, and the reaction time (the residence time in the case of a continuous reaction process) can be appropriately set on the basis of the selectivity to the produced aminoalcohol, as determined by a quantitative analysis means such as gas chromatography. Usually, though, the time is between 0.5 and 20 hours.

A variety of operations can be employed as desired for conducting the hydrogenation reaction in manufacturing method F. This reaction can be conducted without the use of any special apparatus (such as an autoclave). For example, the reaction can be conducted by batch, semi-batch, or continuous process by using a general-purpose apparatus to mix the reaction mixture obtained by the reaction of the cyclic hemiacetal of Formula 1 and the nitrogen-containing compound of Formula 2c with the hydrogenation catalyst by stirring or another such means under a hydrogen gas atmosphere and under the required temperature and hydrogen pressure.

When a reaction mixture obtained by the reaction of the cyclic hemiacetal of Formula 1 and the nitrogen-containing compound of Formula 2c is used for the hydrogenation reaction in manufacturing method F and unreacted cyclic hemiacetal and nitrogen-containing compound remain in this reaction mixture, these unreacted raw materials are sometimes converted into the aminoalcohol of Formula 3c during the hydrogenation reaction. This situation is also encompassed by the present invention.

Upon completion of the hydrogenation reaction, the aminoalcohol of Formula 3c that is the targeted substance can be obtained at a high purity by, for example, removing the hydrogenation catalyst from the obtained reaction mixture by filtration, centrifugation, or the like, and then subjecting the resulting mixture to distillation, crystallization, column chromatography, or another such separation and purification process. Unreacted nitrogen-containing compound can be recovered for reuse.

The aminoalcohol of Formula 3c obtained by manufacturing methods E and F as described above is an aminoalcohol classified as a primary or secondary amine, having an organic group composed of a carbon-skeleton main chain including four or five carbon atoms and linking a hydroxyl group to the nitrogen atom of the amino group. Because of its chemical structure, this aminoalcohol can be used in a wide range of applications as a fiber auxiliary, an emulsifier, a plasticizer, a gas absorbent, a rustproofing agent, a cosmetic raw material, a synthetic detergent, a shoe polish, a glazing agent, a wax, a surfactant, an additive for cutting oil, an additive for lubricating oil, a pesticide additive, an organic solvent, a pH regulator, a neutralizer, an urethanation catalyst, or the like. Also, if the hydroxyl groups are acrylated or methacrylated, this aminoalcohol will be useful as a raw material for acrylic resins, thermoplastic elastomers, resin modifiers, pressure-sensitive adhesives, ion exchange resins, fiber treatment agents, UV-curing inks, paints, and adhesives, electron beam-curing inks, paints, and adhesives, radiation-curing inks, paints, and adhesives, and so forth.

Of the aminoalcohols of Formula 3c obtained by manufacturing methods E and F, aminoalcohol of Formula 3c"

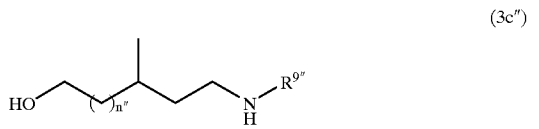

(3c")

(where n" is 0 or 1, $R^{9"}$ is a hydrogen atom or a methyl group when n" is 1, and $R^{9"}$ is a methyl group when n' is 0), that is, 5-amino-3-methyl-1-pentanol, 4-(methylamino)-2-methyl-1-butanol and 5-(methylamino)-3-methyl-1-pentanol are novel compounds which can be expected to find use in a wide range of fields.

EXAMPLES

The present invention will now be described in specific terms through examples.

Examples 1 to 12 are specific examples of manufacturing method A, while Examples 13 to 15 are specific examples of manufacturing method B. Examples 16 to 18 are specific examples of manufacturing method C, while Example 19 is a specific example of manufacturing method D. Examples 20 to 26 are specific examples of manufacturing method E, while Examples 27 and 28 are specific examples of manufacturing method F.

Example 1

Reaction of 2-hydroxy-4-methyltetrahydropyran, dimethylamine, and hydrogen 60 g of a 50 wt % aqueous dimethylamine solution (made by Wako Pure Chemicals Industries; dimethylamine content: 667 mmol) and 650 mg of 5% palladium carbon (hydrogenation catalyst) were put into an electromagnetically stirred autoclave with a 300 mL internal volume and equipped with a gas introduction port and a sampling port. The interior atmosphere was replaced with hydrogen gas, after which the temperature was raised to 80° C. At the point when 80° C. was reached, the pressure was approximately 3.5 atm (gauge pressure). The pressure inside the autoclave was raised to 5 atm (gauge pressure) by introducing hydrogen gas.

65.0 g (556 mmol) of 2-hydroxy-4-methyltetrahydropyran was supplied into the autoclave over a period of 4 hours. The reaction was matured by allowing it to continue another 6 hours upon completion of the supply of 2-hydroxy-4-methyltetrahydropyran. The hydrogen consumed in the reaction was replenished by constantly supplying hydrogen gas during these reaction periods so that the pressure inside the autoclave would be kept at 5 atm (gauge pressure). Also, the reaction temperature was maintained at 80° C. during these periods.

Upon completion of the reaction, the autoclave was cooled and the contents taken out, and the palladium carbon was removed by filtration to obtain a filtrate. This filtrate was analyzed by gas chromatography, which revealed that 76.6 g (528 mmol) of 5-(dimethylamino)-3-methyl-1-pentanol (100% conversion, 95% selectivity, 95% yield) was contained, with no peak observed for the raw material 2-hydroxy-4-methyltetrahydropyran. The analysis conditions in gas chromatography were as follows.

Column: G-300 (trade name of Chemicals Evaluation and Research Institute, Japan)

Column temperature: The temperature was held at 100° C. for 4 minutes, then raised to 220° C. at a rate of 12° C./minute.

Detector: FID

The filtrate obtained above was refined by distillation, which yielded 72.0 g of 5-(dimethylamino)-3-methyl-1-pentanol (boiling point: 74° C. (2 mmHg)).

Examples 2 to 7

Reaction of 2-hydroxy-4-methyltetrahydropyran, a Secondary Amine, and Hydrogen

Other than using the types of secondary amine shown in Table 1 in unmodified form (not an aqueous solution) instead of the aqueous dimethylamine solution, and employing the conditions shown in Table 1 for the usage amount of 2-hydroxy-4-methyltetrahydropyran, the usage amount of secondary amine, the usage amount of palladium carbon, the pressure of the hydrogen gas, the temperature and required time in the addition of the 2-hydroxy-4-methyltetrahydropyran, and the temperature and required time in the maturing of the reaction after this addition, reactions and after-treatments were carried out as in Example 1.

As a result, in every case a corresponding aminoalcohol was obtained at the yield shown in Table 2 (calculated on the basis of 2-hydroxy-4-methyltetrahydropyran). Table 2 also shows the boiling point (temperature and pressure) and $^1$H-NMR (60 MHz) data for the obtained aminoalcohol.

TABLE 1

| Ex. No. | Secondary amine Type | Secondary amine Amount used | 2H4M Amount used | PC Amount used | Hydrogen Pressure (gauge) | Addn. cond. Temp. | Addn. cond. Time | RMC Temp. | RMC Time |
|---|---|---|---|---|---|---|---|---|---|
| 2 | diethylamine | 70.2 g 0.96 mol | 93.6 g 0.80 mol | 0.8 g | 5.0 atm | 80° C. | 3.0 hrs. | 80° C. | 3.0 hrs |
| 3 | dibutylamine | 92.9 g 0.72 mol | 70.2 g 0.60 mol | 0.8 g | 5.0 atm | 80° C. | 3.0 hrs. | 80° C. | 3.0 hrs |
| 4 | N-methylaniline | 77.0 g 0.72 mol | 70.2 g 0.60 mol | 1.5 g | 8.0 atm | 100° C. | 3.0 hrs. | 120° C. | 9.0 hrs |
| 5 | piperidine | 81.7 g 0.96 mol | 93.6 g 0.80 mol | 0.9 g | 5.0 atm | 100° C. | 3.0 hrs | 100° C. | 3.0 hrs |
| 6 | morpholine | 83.6 g 0.96 mol | 93.6 g 0.80 mol | 0.9 g | 5.0 atm | 100° C. | 3.0 hrs | 100° C. | 3.0 hrs |
| 7 | 2-(methylamino)-1-ethanol | 72.1 g 0.96 mol | 93.6 g 0.80 mol | 0.8 g | 5.0 atm | 100° C. | 3.0 hrs | 100° C. | 2.0 hrs |

2H4M: 2-hydroxy-4-methyltetrahydropyran
PC: palladium carbon
Addn. cond.: Addition conditions
RMC: Reaction maturing conditions

TABLE 2

| Example No. | Name of produced aminoalcohol | Isolated yield (%) | Boiling point | $^1$H-NMR (60 MHz) |
|---|---|---|---|---|
| 2 | 5-(diethylamino)-3-methyl-1-pentanol | 89 | 83° C. 2.0 torr | δ: 0.85–1.84 (m; 14H), 2.30–2.80 (m; 6H), 3.60 (t; 2H, J = 6 Hz), 4.12 (s; 1H) |
| 3 | 5-(dibutylamino)-3-methyl-1-pentanol | 85 | 111° C. 1.5 torr | δ: 0.77–2.05 (m; 22H), 2.25–2.75 (m; 6H), 3.22 (s; 1H), 3.65 (t; 2H) |
| 4 | 5-(N-phenylmethylamino)-3-methyl-1-pentanol | 65 | 138° C. 3.5 torr | δ: 0.79–2.02 (m; 8H), 2.84 (s; 3H), 3.10–3.83 (m; 5H), 6.50–7.37 (m; 5H) |
| 5 | 1-(5-hydroxy-3-methylpentyl)piperidine | 90 | 116° C. 2.0 torr | δ: 0.93 (d; 3H, J = 5 Hz), 1.15–1.98 (m; 11H), 2.16–2.64 (m; 6H), 3.65 (t; 2H, J = 6 Hz), 3.89 (s; 1H) |
| 6 | 4-(5-hydroxy-3-methylpentyl)morpholine | 89 | 114° C. 2.0 torr | δ: 0.94 (d; 3H, J = 6 Hz), 1.15–1.98 (m; 5H), 2.24–2.63 (m; 6H), 3.37 (s; 1H), 3.50–3.92 (m; 6H) |
| 7 | 5-(N-methyl(2-hydroxyethyl)amino)-3-methyl-1-pentanol | 82 | 131° C. 2.0 torr | δ: 0.80–2.01 (m; 8H), 2.20–2.68 (m; 7H), 3.45–3.82 (m; 6H) |

Reference Example 1

Manufacture of 5,5-dimethyl-2-hydroxytetrahydrofuran 41.3 mg (0.16 mmol) of Rh(acac) (CO)$_2$, 1296 mg (2.0 mmol) of tris(2,4-di-t-butylphenyl)phosphite, 298 mg (2.0 mmol) of triethanolamine, 68.2 mg (0.16 mmol) of diphenylphosphinobutane, 20 mL of toluene, and 313 g (380 mL, 3.6 mol) of 2-methyl-3-buten-2-ol were kept away from air while being supplied into an electromagnetically stirred autoclave with a 500 mL internal volume and equipped with a gas introduction port and a sampling port. A mixed gas of hydrogen and carbon monoxide (molar ratio of hydrogen/carbon monoxide=1/1) was then supplied to keep the internal pressure at 100 atm (gauge pressure). The temperature inside the autoclave was raised to 80° C. over a period of 30 minutes while the system was stirred at a rate of 1000 rpm. The reaction was conducted for 10 hours at a temperature of 80° C. under stirring while the internal pressure was held at 100 atm (gauge pressure) by constantly supplying mixed gas of hydrogen and carbon monoxide (molar ratio of hydrogen/carbon monoxide=1/1).

The reaction mixture thus obtained was analyzed by gas chromatography, which revealed that the conversion of 2-methyl-3-buten-2-ol was 99% and that the mixture contained 355 g of 5,5-dimethyl-2-hydroxytetrahydrofuran (85% selectivity and 84% yield). The gas chromatography analysis conditions were as follows.

Column: G-300 (trade name of Chemicals Evaluation and Research Institute, Japan)
Column temperature: The temperature was held at 80° C. for 2 minutes, then raised to 220° C. at a rate of 10° C./minute.
Detector: FID An evaporator was used to remove the raw materials and low-boiling by-products under reduced pressure from the reaction mixture obtained above. The residue thus obtained was subjected to reduced pressure distillation. The distillate (300 g) obtained at a pressure (absolute pressure) of 10 KPa and a temperature of 54° C. was analyzed by gas chromatography, which revealed this liquid to be a mixture of 269 g (2.3 mol) of 5,5-dimethyl-2-hydroxytetrahydrofuran and 23.9 g (0.08 mol) of 2,3-dimethyl-3-hydroxybutyraldehyde.

Examples 8 to 12

Reaction of a cyclic hemiacetal, a secondary amine, and hydrogen

A secondary amine of the type shown in Table 3 below and 5% palladium carbon (hydrogenation catalyst) were put in the amounts shown in Table 3 into an electromagnetically stirred autoclave with a 300 mL internal volume and equipped with a gas introduction port and a sampling port. The interior atmosphere was replaced with hydrogen gas, after which the temperature was raised to 80° C. The pressure inside the autoclave was then raised to 5 atm (gauge pressure) by introducing hydrogen gas.

A cyclic hemiacetal was supplied to the autoclave over a period of 4 hours in the type and amount shown in Table 3. The reaction was mature by continuing the reaction for another 4 hours upon completion of the cyclic hemiacetal supply. The hydrogen consumed in the reaction was replenished by constantly supplying hydrogen gas during these reaction periods so that the pressure inside the autoclave would be kept at 5 atm (gauge pressure). Also, the reaction temperature was maintained at 80° C. during these periods.

Upon completion of the reaction, the autoclave was cooled and the contents taken out, and the palladium carbon was removed by filtration to obtain a filtrate. This filtrate was refined by distillation, whereupon a corresponding aminoalcohol was obtained at the yield shown in Table 4 (calculated on the basis of cyclic hemiacetal). Table 4 also shows the boiling point (temperature and pressure) and $^1$H-NMR (60 MHz) data for the obtained aminoalcohol.

TABLE 3

| Ex. No. | Secondary amine | | Cyclic hemiacetal | | Palladium carbon Amount used |
|---|---|---|---|---|---|
| | Type | Amount used | Type | Amount used | |
| 8 | dimethylamine (aqueous solution) | 74 g (aqueous solution) 0.82 mol (amine) | 2-hydroxytetra-hydrofuran | 60 g 0.68 mol | 1.3 g |
| 9 | diethylamine | 90 g 1.2 mol | 2-hydroxytetra-hydrofuran | 90 g 1.0 mol | 1.8 g |
| 10 | dimethylamine (aqueous solution) | 83 g (aqueous solution) 0.92 mol (amine) | 2-hydroxy-4-methyltetra-hydrofuran | 78 g 0.76 mol | 1.6 g |
| 11 | diethylamine | 83 g 1.1 mol | 2-hydroxy-4-methyltetra-hydrofuran | 97 g 0.95 mol | 1.8 g |
| 12 | dimethylamine (aqueous solution) | 76 g (aqueous solution) 0.85 mol (amine) | 5,5-dimethyl-2-hydroxytetra-hydrofuran | 84 g 0.71 mol | 1.6 g |

TABLE 4

| Ex. No. | Name of produced aminoalcohol | Isolated yield (%) | Boiling point | $^1$H-NMR (60 MHz) |
|---|---|---|---|---|
| 8 | 4-(dimethylamino)-1-butanol | 88 | 81° C. 10 torr | — |
| 9 | 4-(diethylamino)-1-butanol | 90 | 99° C. 10 torr | δ: 1.01 (t; 6H, J = 7 Hz), 1.50–1.92 (m; 4H), 2.25–2.85 (m; 8H), 3.34–3.78 (m; 6H), 6.20 (s; 1H) |
| 10 | 4-(dimethylamino)-2-methyl-1-butanol | 93 | 54° C. 1.0 torr | δ: 0.89 (d; 3H, J = 6 Hz), 1.30–1.98 (m; 6H), 2.23–2.67 (m; 8H), 3.25–3.60 (m; 2H), 5.80 (s; 1H) |
| 11 | 4-(diethylamino)-2-methyl-1-butanol | 90 | 64° C. 1.0 torr | δ: 0.78–2.10 (m; 12 H), 2.33–2.98 (m; 6H), 3.03–3.57 (m; 2H), 6.70 (s; 1H) |
| 12 | 5-(dimethylamino)-2-methyl-2-pentanol | 88 | 54° C. 1.0 torr | δ: 1.18 (s; 6H), 1.49–2.03 (m; 4H), 2.13–2.60 (m; 8H), 5.46 (s; 1H) |

Example 13

(1) (Reaction of 2-hydroxy-4-methyltetrahydropyran and dimethylamine)

The atmosphere inside a glass three-necked flask with a 500 mL internal volume and equipped with a stirrer was replaced with nitrogen gas, after which 155 g (1.28 mol) of 2-hydroxy-4-methyltetrahydropyran was put in, and the temperature of the liquid on the inside was lowered to 2° C. by cooling in an ice-water bath. It took 30 minutes to absorb 90.5 g (2.01 mol) of dimethylamine while maintaining the temperature of the liquid inside at 10° C. or lower by supplying gaseous dimethylamine into the liquid on the inside. The system was stirred for another 30 minutes at 10° C., after which the stirring was continued for 1 hour at 25° C.

Upon completion of the stirring, the reaction mixture was analyzed by gas chromatography, whereupon the peak for the raw material 2-hydroxy-4-methyltetrahydropyran was only observed in an amount equivalent to 0.5 g (99.7% conversion). The water was removed from this reaction mixture under reduced pressure, and the concentrate thus obtained was refined by distillation, whereupon 132 g of 2-(dimethylamino)-4-methyltetrahydropyran was obtained (boiling point: 52° C. (4.0 mmHg); isolated yield: 72%). The $^1$H-NMR data for the obtained 2-(dimethylamino)-4-methyltetrahydropyran was as follows.

δ (ppm): 0.91–1.81 (m; 8H), 2.39 (s; 6H), 3.13–4.23 (m; 3H)

(2) (Hydrogenation of 2-(dimethylamino)-4-methyltetrahydropyran)

50 mL (46.3 g, 0.32 mol) of the obtained 2-(dimethylamino)-4-methyltetrahydropyran was put into an electromagnetically stirred autoclave with a 300 mL internal volume and equipped with a gas introduction port and a sampling port, along with 50 mL of isopropyl alcohol and 1.0 g of 5% palladium carbon (hydrogenation catalyst). The atmosphere on the inside was replaced with hydrogen gas, after which the temperature was raised to 80° C. while the pressure was held at approximately 5.0 atm (gauge pressure) by supplying hydrogen gas. After 80° C. had been reached, a reaction was conducted for 3 hours while the temperature was kept between 80 and 90° C. During this reaction period, the pressure inside the autoclave was maintained at 5 atm (gauge pressure) by constantly supplying hydrogen gas.

Upon completion of the reaction, the autoclave was cooled and the contents taken out, and the palladium carbon was removed by filtration to obtain a filtrate. This filtrate was analyzed by gas chromatography, which revealed that 46.6 g (0.32 mmol) of 5-(dimethylamino)-3-methyl-1-pentanol (100% conversion, 99% selectivity) was contained, with no peak observed for the raw material 2-(dimethylamino)-4-methyltetrahydropyran.

Example 14

(1) (Reaction of 2-hydroxy-4-methyltetrahydropyran and dibutylamine)

The atmosphere inside a glass three-necked flask with a 500 mL internal volume and equipped with a stirrer, a reflux condenser and a Dean-Stark equipment was replaced with nitrogen gas, after which 200 mL of toluene, 61.1 g (95% purity, 0.50 mol) of 2-hydroxy-4-methyltetrahydropyran, and 77.4 g (0.60 mol) of dibutylamine were put in, after which 0.6 g of p-toluenesulfonic acid was added. The mixed solution of these was heated to an internal temperature of 128° C. in an oil bath, and a state of refluxed toluene was maintained. The toluene reflux was conducted for 2 hours while water was removed in the form of an azeotropic mixture with the Dean-Stark equipment.

Upon completion of the heating and reflux, the obtained reaction mixture was analyzed by gas chromatography, which revealed only a trace amount in the peak for the raw material 2-hydroxy-4-methyltetrahydropyran (100% conversion). The toluene was removed from this reaction mixture under reduced pressure, and the concentrate thus obtained was refined by distillation, whereupon 93.0 g (0.41 mol) of 2-(dibutylamino)-4-methyltetrahydropyran was obtained (boiling point: 84° C. (2.0 mmHg); isolated yield: 82%). The $^1$H-NMR data for the obtained 2-(dibutylamino)-4-methyltetrahydropyran was as follows.

δ (ppm): 0.71–1.81 (m; 22H), 2.46–2.93 (m; 4H), 3.10–4.19 (m; 3H)

(2) (Hydrogenation of 2-(dibutylamino)-4-methyltetrahydropyran)

50 mL (43.1 g, 0.19 mol) of the obtained 2-(dibutylamino)-4-methyltetrahydropyran was put into an electromagnetically stirred autoclave with a 300 mL internal volume and equipped with a gas introduction port and a sampling port, along with 50 mL of isopropyl alcohol and 1.0 g of 5% palladium carbon (hydrogenation catalyst). The atmosphere on the inside was replaced with hydrogen gas, after which the temperature was raised to 80° C. while the pressure was held at approximately 5.0 atm (gauge pressure) by supplying hydrogen gas. After 80° C. had been reached, a reaction was conducted for 3 hours while the temperature was kept between 80 and 90° C. During this reaction period, the pressure inside the autoclave was maintained at 5 atm (gauge pressure) by constantly supplying hydrogen gas.

Upon completion of the reaction, the autoclave was cooled and the contents taken out, and the palladium carbon was removed by filtration to obtain a filtrate. This filtrate was analyzed by gas chromatography, which revealed that 43.2 g (0.32 mmol) of 5-(dibutylamino)-3-methyl-1-pentanol (100% conversion, 99% selectivity) was contained, with no peak observed for the raw material 2-(dibutylamino)-4-methyltetrahydropyran.

Example 15

(1) (Reaction of 2-hydroxy-4-methyltetrahydrofuran and dimethylamine)

The atmosphere inside a glass three-necked flask with a 300 mL internal volume and equipped with a stirrer was replaced with nitrogen gas, after which 59.5 g (0.58 mol) of 2-hydroxy-4-methyltetrahydrofuran and 32.0 g of molecular sieves were put in, and the temperature of the liquid on the inside was lowered to 2° C. by cooling in an ice-water bath. It took 10 minutes to absorb 39.4 g (0.87 mol) of dimethylamine while maintaining the temperature of the liquid inside at 10° C. or lower by supplying gaseous dimethylamine into the liquid being stirred on the inside. The system was stirred for another 30 minutes at 10° C. after this absorption.

Upon completion of the stirring, the reaction mixture was analyzed by gas chromatography, whereupon the peak for the raw material 2-hydroxy-4-methyltetrahydrofuran was only observed in an amount equivalent to 1.5 g (97.5% conversion). The molecular sieves were removed by filtering this reaction mixture, after which the filtrate thus obtained was refined by distillation, whereupon 49.0 g of 2-(dimethylamino)-4-methyltetrahydrofuran was obtained (boiling point: 58° C. (25 mmHg); isolated yield: 65%). The $^1$H-NMR data for the obtained 2-(dimethylamino)-4-methyltetrahydrofuran was as follows.

δ (ppm): 1.01 (d; 3H, J=6 Hz), 1.26–2.54 (m; 2H), 2.33 (s; 6H), 2.70–4.78 (m; 4H)

(2) (Hydrogenation of 2-(dimethylamino)-4-methyltetrahydrofuran)

50 mL (44.6 g, 0.35 mol) of the obtained 2-(dimethylamino)-4-methyltetrahydrofuran was put into an electromagnetically stirred autoclave with a 300 mL internal volume and equipped with a gas introduction port and a sampling port, along with 50 mL of isopropyl alcohol and 1.0 g of 5% palladium carbon (hydrogenation catalyst). The atmosphere on the inside was replaced with hydrogen gas, after which the temperature was raised to 80° C. while the pressure was held at approximately 5.0 atm (gauge pressure) by supplying hydrogen gas. After 80° C. had been reached, a reaction was conducted for 3 hours while the temperature was kept between 80 and 90° C. During this reaction period, the pressure inside the autoclave was maintained at 5 atm (gauge pressure) by constantly supplying hydrogen gas.

Upon completion of the reaction, the autoclave was cooled and the contents taken out, and the palladium carbon was removed by filtration to obtain a filtrate. This filtrate was analyzed by gas chromatography, which revealed that 44.7 g (0.34 mmol) of 4-(dimethylamino)-2-methyl-1-butanol (100% conversion, 99% selectivity) was contained, with no peak observed for the raw material 2-(dimethylamino)-4-methyltetrahydrofuran.

Manufacturing methods A and B illustrated in Examples 1 to 15 above allow an aminoalcohol classified as a tertiary amine and in which the hydroxyl group and amino group are four or five carbon atoms apart to be manufactured at a high yield from raw materials that are readily available and easy to handle. Furthermore, no special reaction apparatus, special reaction conditions, or complicated after-treatment operation is required. Therefore, the present invention provides a method with which the above-mentioned aminoalcohol can be manufactured in advantageously in an industrial setting.

Example 16

Reaction of 2-hydroxy-4-methyltetrahydropyran, methylamine, and hydrogen 41 g of a 40 wt % aqueous methylamine solution (methylamine content: 530 mmol) and 1.80 g of 5% palladium carbon (hydrogenation catalyst) were put into an electromagnetically stirred autoclave with a 300 mL internal volume and equipped with a gas introduction port and a sampling port. The interior atmosphere was replaced with hydrogen gas, after which the temperature was raised to 80° C. At the point when 80° C. was reached, the pressure was approximately 3.8 atm (gauge pressure). The pressure inside the autoclave was raised to 5 atm (gauge pressure) by introducing hydrogen gas.

139 g (1160 mmol) of 2-hydroxy-4-methyltetrahydropyran was supplied into the autoclave over a period of 4 hours. The reaction was matured by allowing it to continue another 6 hours upon completion of the supply of 2-hydroxy-4-methyltetrahydropyran. The hydrogen consumed in the reaction was replenished by constantly supplying hydrogen gas during these reaction periods so that the pressure inside the autoclave would be kept at 5 atm (gauge pressure). Also, the reaction temperature was maintained at 80° C. during these periods.

Upon completion of the reaction, the autoclave was cooled and the contents taken out, and the palladium carbon was removed by filtration to obtain a filtrate. This filtrate was analyzed by gas chromatography, which revealed that 106.0 g (493 mmol) of N,N-bis(5-hydroxy-3-methylpentyl)methylamine (100% conversion on the basis of the methylamine used, 93% selectivity, 93% yield) was contained, with no peak observed for the raw material methylamine. The analysis conditions in gas chromatography were as follows.

Column: G-100 (trade name of Chemicals Evaluation and Research Institute, Japan)

Column temperature: The temperature was held at 100° C. for 4 minutes, then raised to 280° C. at a rate of 16° C./minute.

Detector: FID

The filtrate obtained above was refined by distillation, which yielded 92.0 g of N,N-bis(5-hydroxy-3-methylpentyl)methylamine (boiling point: 165° C. (4.5 mmHg)). The $^1$H-NMR (60 MHz) data for the obtained N,N-bis(5-hydroxy-3-methylpentyl)methylamine was as follows.

δ (ppm): 0.92 (d; 6H, J=6 Hz), 0.73–2.04 (m; 10H), 2.16 (s; 3H), 2.35 (t; 4H, J=7 Hz), 3.63 (t; 4H, J=6 Hz), 3.98 (s; 2H)

Example 17

Reaction of 2-hydroxy-4-methyltetrahydropyran, Butylamine, and Hydrogen 40 g (548 mmol) of butylamine and 1.80 g of 5% palladium carbon (hydrogenation catalyst) were put into an electromagnetically stirred autoclave with a 300 mL internal volume and equipped with a gas introduction port and a sampling port. The interior atmosphere was replaced with hydrogen gas, after which the temperature was raised to 80° C. At the point when 80° C. was reached, the pressure inside the autoclave was raised to 5 atm (gauge pressure) by introducing hydrogen gas.

140 g (1170 mmol) of 2-hydroxy-4-methyltetrahydropyran was supplied into the autoclave over a period of 4 hours. The reaction was continued another 2 hours at 80° C. upon completion of the supply of 2-hydroxy-4-methyltetrahydropyran. The reaction was then matured by allowing it to continue another 2 hours at 100° C. The hydrogen consumed in the reaction was replenished by constantly supplying hydrogen gas during these reaction periods so that the pressure inside the autoclave would be kept at 5 atm (gauge pressure).

Upon completion of the reaction, the autoclave was cooled and the contents taken out, and the palladium carbon was removed by filtration to obtain a filtrate. This filtrate was analyzed by gas chromatography, which revealed that 139 g (509 mmol) of N,N-bis(5-hydroxy-3-methylpentyl)butylamine (100% conversion on the basis of the butylamine used, 93% selectivity, 93% yield) was contained, with no peak observed for the raw material butylamine.

The filtrate obtained above was refined by distillation, which yielded 130 g of N,N-bis(5-hydroxy-3 -methylpentyl)butylamine (boiling point: 175° C. (1.0 mmHg)). The $^1$H-NMR (60 MHz) data for the obtained N,N-bis(5-hydroxy-3-methylpentyl)butylamine was as follows.

δ (ppm): 0.67–2.72 (m; 23H), 2.07–2.74 (m; 6H), 3.37–3.90 (m; 4H), 4.14 (s; 2H)

Example 18

Reaction of 2-hydroxy-4-methyltetrahydrofuran, methylamine, and hydrogen 41 g of a 40 wt % aqueous methylamine solution (methylamine content: 530 mmol) and 1.60 g of 5% palladium carbon (hydrogenation catalyst) were put into an electromagnetically stirred autoclave with a 300 mL internal volume and equipped with a gas introduction port and a sampling port. The interior atmosphere was replaced with hydrogen gas, after which the temperature was raised to 80° C. At the point when 80° C. was reached, the pressure inside the autoclave was raised to 5 atm (gauge pressure) by introducing hydrogen gas.

119 g (1160 mmol) of 2-hydroxy-4-methyltetrahydrofuran was supplied into the autoclave over a period of 4 hours. The reaction was matured by allowing it to continue another 2 hours upon completion of the supply of 2-hydroxy-4-methyltetrahydrofuran. The hydrogen consumed in the reaction was replenished by constantly supplying hydrogen gas during these reaction periods so that the pressure inside the autoclave would be kept at 5 atm (gauge pressure). Also, the reaction temperature was maintained at 80° C. during these periods.

Upon completion of the reaction, the autoclave was cooled and the contents taken out, and the palladium carbon was removed by filtration to obtain a filtrate. This filtrate was analyzed by gas chromatography, which revealed that 104 g (514 mmol) of N,N-bis(4-hydroxy-3-methylbutyl)methylamine (100% conversion on the basis of the methylamine used, 97% selectivity, 97% yield) was contained, with no peak observed for the raw material methylamine.

The filtrate obtained above was refined by distillation, which yielded 99.4 g of N,N-bis(4-hydroxy-3-methylbutyl)methylamine (boiling point: 137° C. (3.0 mmHg)). The $^1$H-NMR (60 MHz) data for the obtained N,N-bis(4-hydroxy-3-methylbutyl)methylamine was as follows.

δ (ppm): 0.91 (d; 6H, J=6 Hz), 0.65–2.02 (m; 6H), 2.23 (s; 3H), 2.42 (t; 4H, J=6 Hz), 3.37 (d; 4H, J=5 Hz), 5.61 (s; 2H)

Example 19

(1) (Reaction of 2-hydroxy-4-methyltetrahydropyran and butylamine)

The atmosphere inside a glass three-necked flask with a 300 mL internal volume and equipped with a stirrer was replaced with nitrogen gas, after which 52.9 g (440 mmol) of 2-hydroxy-4-methyltetrahydropyran and 30 g of molecular sieves were put in, and the temperature of the liquid on the inside was lowered to 2° C. by cooling in an ice-water bath. 14.6 g (200 mmol) of butylamine was supplied dropwise into the liquid on the inside under agitation over a period of 5 minutes while the temperature of the liquid inside was maintained at 10° C. or lower. The system was stirred for another 30 minutes at 10° C. after completion of the dropping.

Upon completion of the stirring, the solution part of the reaction mixture thus obtained was analyzed by gas chromatography, whereupon no peak was observed for the raw material butylamine (100% conversion). The molecular sieves were removed by filtering the reaction mixture, and 54.1 g of filtrate was obtained.

(2) (Hydrogenation of obtained reaction mixture)

20 g of the obtained filtrate was put into an electromagnetically stirred autoclave with a 300 mL internal volume and equipped with a gas introduction port and a sampling port, along with 80 mL of isopropyl alcohol and 2.0 g of 5% palladium carbon (hydrogenation catalyst). The atmosphere on the inside was replaced with hydrogen gas, after which the temperature was raised to 80° C. while the pressure was held at approximately 8.0 atm (gauge pressure) by supplying hydrogen gas. A reaction was conducted for 2 hours while the temperature was kept at 80° C. The reaction was matured by raising the temperature to 100° C. and allowing the reaction to continue for another 4 hours. The pressure inside the autoclave was maintained at 8.0 atm (gauge pressure) by constantly supplying hydrogen gas during these reaction periods.

Upon completion of the reaction, the autoclave was cooled and the contents taken out, and the palladium carbon was removed by filtration to obtain a filtrate. This filtrate was analyzed by gas chromatography, which revealed that 17.6 g (64 mmol) of N,N-bis(5-hydroxy-3-methylpentyl)butylamine had been produced (87% yield based on the butylamine used).

Manufacturing methods C and D illustrated in Examples 16 to 19 above allow an aminoalcohol classified as a tertiary amine, and in which at least two of the three organic groups bonded to nitrogen atom have a chemical structure such that hydroxyl groups are bonded to the nitrogen atom via a carbon skeleton composed of four or five carbon atoms, to be manufactured at a high yield from raw materials that are readily available and easy to handle. Furthermore, no special reaction apparatus, special reaction conditions, or complicated after-treatment operation is required. Therefore, the present invention provides a method with which the above-mentioned aminoalcohol can be manufactured in advantageously in an industrial setting.

Example 20

Reaction of 2-hydroxy-4-methyltetrahydropyran, ammonia, and hydrogen 1.7 g of Raney nickel, 36.0 g of 2-hydroxy-4-methyltetrahydropyran (95% purity, 295 mmol), 100 g of a 25% aqueous ammonia solution (1470 mmol as ammonia, 5 times (molar) with respect to 2-hydroxy-4-methyltetrahydropyran), and 30 g of 1-octanol were put into an electromagnetically stirred autoclave with a 300 mL internal volume and equipped with a gas introduction port and a sampling port. The interior atmosphere was replaced with hydrogen gas, after which the hydrogen pressure was raised to 2.0 atm (gauge pressure), and then the temperature was raised to 80° C. At the point when 80° C. was reached, the pressure inside the autoclave was approximately 3.0 atm (gauge pressure). The pressure inside the autoclave was raised to 5 atm (gauge pressure) by introducing hydrogen gas.

The reaction was matured by allowing it to continue in this state for 6 hours. The hydrogen consumed in the reaction was replenished by constantly supplying hydrogen gas during these reaction periods so that the pressure inside the autoclave would be kept at 5 atm (gauge pressure). Also, the reaction temperature was maintained at 80° C. during these periods.

Upon completion of the reaction, the autoclave was cooled and the contents taken out, and the Raney nickel was removed by filtration to obtain a filtrate. This filtrate was analyzed by gas chromatography, which revealed that 32.1 g (274 mmol) of 5-amino-3-methyl-1-pentanol (100% conversion on the basis of the 2-hydroxy-4-methyltetrahydropyran used, 93% selectivity, 93% yield) was contained, with no peak observed for the raw material 2-hydroxy-4-methyltetrahydropyran. The analysis conditions in gas chromatography were as follows.

Column: G-300 (trade name of Chemicals Evaluation and Research Institute, Japan)

Column temperature: The temperature was held at 100° C. for 4 minutes, then raised to 220° C. at a rate of 12° C./minute.

Detector: FID

The filtrate obtained above was refined by distillation, which yielded 18.6 g of 5-amino-3-methyl-1-pentanol (boiling point: 101° C. (0.8 mmHg)). The NMR data for this compound was as follows.

$^1$H-NMR: δ (ppm): 0.91 (d; 3H, J=6 Hz), 1.23–1.79 (m; 5H), 2.18 (s; 3H), 2.64–2.83 (m; 2H), 3.56–3.73 (m; 2H)

Example 21

Reaction of 2-hydroxy-4-methyltetrahydrofuran, ammonia, and hydrogen

Other than using 30.1 g (295 mmol) of 2-hydroxy-4-methyltetrahydrofuran in place of 2-hydroxy-4-methyltetrahydropyran, the reaction and after-treatment were carried out according to Example 20. As a result, 28.0 g (271 mmol) of 4-amino-2-methyl-1-butanol (100% conversion on the basis of the 2-hydroxy-4-methyltetrahydrofuran used, 92% selectivity, 92% yield) was contained, with no peak observed for the raw material 2-hydroxy-4-methyltetrahydrofuran.

Example 22

Reaction of 2-hydroxy-4-methyltetrahydrofuran, ammonia, and hydrogen 1.2 g of Raney nickel, 62.0 g (608 mmol) of 2-hydroxy-4-methyltetrahydrofuran, and 62.0 g of a 25% aqueous ammonia solution (912 mmol as ammonia, 1.5 times (molar) with respect to 2-hydroxy-4-methyltetrahydrofuran) were put into an electromagnetically stirred autoclave with a 300 mL internal volume and equipped with a gas introduction port and a sampling port. The interior atmosphere was replaced with hydrogen gas, after which the hydrogen pressure was raised to 2.0 atm (gauge pressure) and the temperature was raised to 80° C. At the point when 80° C. was reached, the pressure inside the autoclave was approximately 3.0 atm (gauge pressure). The pressure inside the autoclave was raised to 5 atm (gauge pressure) by introducing hydrogen gas.

The reaction was matured by allowing it to continue in this state for 8 hours. The hydrogen consumed in the reaction was replenished by constantly supplying hydrogen gas during these reaction periods so that the pressure inside the autoclave would be kept at 5 atm (gauge pressure). Also, the reaction temperature was maintained at 80° C. during these periods.

Upon completion of the reaction, the autoclave was cooled and the contents taken out, and the Raney nickel was removed by filtration to obtain a filtrate. This filtrate was analyzed by gas chromatography, which revealed that 55.1 g (535 mmol) of 4-amino-2-methyl-1-butanol (100% conversion on the basis of the 2-hydroxy-4-methyltetrahydrofuran used, 88% selectivity, 88% yield) was contained, with no peak observed for the raw material 2-hydroxy-4-methyltetrahydrofuran.

Example 23

Reaction of 2-hydroxy-4-methyltetrahydropyran, ammonia, and hydrogen 4.0 g of a nickel catalyst supported on diatomaceous earth (52% nickel content) and 15 mL of 1-butanol were put into an electromagnetically stirred autoclave with a 300 mL internal volume and equipped with a gas introduction port and a sampling port. The interior of the autoclave was replaced three times with hydrogen gas of 10 atm (gauge pressure). Then 64.2 g (3mmol) of ammonia was added, hydrogen was supplied to make a hydrogen partial pressure 10 atm (gauge pressure), and the temperature of the autoclave was raised to 140° C. The pressure inside the autoclave at this point read 125 atm (gauge pressure). The overall pressure here was raised to 140 atm (gauge pressure) by supplying hydrogen. 65.9 g of 2-hydroxy-4-methyltetrahydropyran (95% purity, 540 mmol) was fed in over a period of 1 hour, and the reaction was then matured over a period of 4 hours. The hydrogen consumed in the reaction was replenished by constantly supplying hydrogen gas during the reaction period after the start of feed of 2-hydroxy-4-methyltetrahydropyran so that the pressure inside the autoclave would be kept at 140 atm (gauge pressure). Also, the reaction temperature was maintained at 140° C. during these periods.

Upon completion of the reaction, the autoclave was cooled, ammonia was liberated, and the contents was taken out, and the Raney nickel was removed by filtration to obtain a filtrate. This filtrate was analyzed by gas chromatography, which revealed that 60.8 g (520 mmol) of 5-amino-3-methyl-1-pentanol (100% conversion on the basis of the 2-hydroxy-4-methyltetrahydropyran used, 96% selectivity, 96% yield) was contained, with no peak observed for the raw material 2-hydroxy-4-methyltetrahydropyran.

Example 24

Reaction of 2-hydroxy-4-methyltetrahydrofuran, ammonia, and hydrogen

Other than using 55.1 g (540 mmol) of 2-hydroxy-4-methyltetrahydrofuran in place of 2-hydroxy-4-methyltetrahydropyran, the reaction was carried out in the same manner as in Example 23.

Upon completion of the reaction, the reaction filtrate was analyzed by gas chromatography, which revealed that 52.7 g (512 mmol) of 4-amino-2-methyl-1-butanol (100% conversion on the basis of the 2-hydroxy-4-methyltetrahydrofuran used, 95% selectivity, 95% yield) was contained, with no peak observed for the raw material 2-hydroxy-4-methyltetrahydrofuran.

Example 25

Reaction of 2-hydroxy-4-methyltetrahydrofuran, Methylamine, and Hydrogen 1.7 g of Raney nickel, 40.0 g of 2-hydroxy-4-methyltetrahydrofuran (95% purity, 373 mmol), and 43.3 g of a 40% aqueous methylamine solution (559 mmol as methylamine, 1.5 times (molar) with respect to 2-hydroxy-4-methyltetrahydrofuran) were put into an electromagnetically stirred autoclave with a 300 mL internal volume and equipped with a gas introduction port and a sampling port. The interior atmosphere was replaced with hydrogen gas, after which the hydrogen pressure was raised to 2.0 atm (gauge pressure) and the temperature was raised to 80° C. At the point when 80° C. was reached, the pressure inside the autoclave was approximately 3.0 atm (gauge pressure). The pressure inside the autoclave was raised to 5 atm (gauge pressure) by introducing hydrogen gas.

The reaction was matured by allowing it to continue in this state for 6 hours. The hydrogen consumed in the reaction was replenished by constantly supplying hydrogen gas during these reaction periods so that the pressure inside the autoclave would be kept at 5 atm (gauge pressure). Also, the reaction temperature was maintained at 80° C. during these periods.

Upon completion of the reaction, the autoclave was cooled and the contents taken out, and the Raney nickel was removed by filtration to obtain a filtrate. This filtrate was analyzed by gas chromatography, which revealed that 40.1 g (343 mmol) of 4-(methylamino)-2-methyl-1-butanol (100% conversion on the basis of the 2-hydroxy-4-methyltetrahydrofuran used, 92% selectivity, 92% yield) was contained, with no peak observed for the raw material 2-hydroxy-4-methyltetrahydrofuran. The analysis conditions in gas chromatography were as follows.

Column: G-300 (trade name of Chemicals

Evaluation and Research Institute, Japan)

Column temperature: The temperature was held at 100° C. for 4 minutes, then raised to 220° C. at a rate of 12° C./minute.

Detector: FID

The filtrate obtained above was refined by distillation, which yielded 28.3 g of 4-(methylamino)-2-methyl-1-butanol (boiling point: 74° C. (2 mmHg)). The NMR data for this compound was as follows.

$^1$H-NMR: δ (ppm): 0.89 (d; 3H, J=6 Hz), 1.64–2.03 (m; 3H), 2.15–2.98 (m; 2H), 2.40 (s; 3H), 3.77 (s; 2H), 3.09–4.17 (m; 2H)

Example 26

Reaction of 2-hydroxy-4-methyltetrahydropyran, Methylamine, and Hydrogen

Other than using 47.5 g (373 mmol) of 2-hydroxy-4-methyltetrahydropyran in place of 2-hydroxy-4-methyltetrahydrofuran, the reaction and after-treatment were carried out according to Example 25. As a result, 43.4 g (332 mmol) of 5-(methylamino)-3-methyl-1-pentanol (100% conversion on the basis of the 2-hydroxy-4-methyltetrahydropyran used, 89% selectivity, 89% yield) was contained, with no peak observed for the raw material 2-hydroxy-4-methyltetrahydropyran.

The filtrate obtained above was refined by distillation, which yielded 31.0 g of 5-(methylamino)-3-methyl-1-pentanol (boiling point: 81° C. (2.0 mmHg)). The NMR data for this compound was as follows.

$^1$H-NMR: δ (ppm): 0.82 (d; 3H, J=6 Hz), 1.04–2.00 (m; 5H), 2.15–2.95 (m; 2H), 2.40 (s; 3H), 2.96 (s; 2H), 3.15–3.77 (m; 2H)

Example 27

(1) (Reaction of 2-hydroxy-4-methyltetrahydropyran and butylamine)

The atmosphere inside a glass three-necked flask with a 300 mL internal volume and equipped with a stirrer was replaced with nitrogen gas, after which 118 g (975 mmol) of 2-hydroxy-4-methyltetrahydropyran and 60 g of molecular sieves were put in, and the temperature of the liquid on the inside was lowered to 2° C. by cooling in an ice-water bath. 87.8 g (1200 mmol) of butylamine was supplied dropwise into the liquid on the inside under agitation over a period of 5 minutes while the temperature of the liquid inside was maintained at 10° C. or lower. The system was stirred for another 30 minutes at 10° C. after completion of the dropping.

Upon completion of the stirring, the solution part of the reaction mixture thus obtained was analyzed by gas chromatography, which revealed that 3.3 g of the raw material 2-hydroxy-4-methyltetrahydropyran was contained (97% conversion). This reaction mixture was filtered to remove the molecular sieves and obtain 210 g of filtrate.

The filtrate obtained above was refined by distillation, which yielded 125 g of a fraction containing 94.6% 2-(butylamino)-4-methyltetrahydropyran (boiling point: 94–8° C. (9.0 mmHg)). The NMR data for this compound was as follows.

$^1$H-NMR: δ (ppm): 0.70–2.10 (m; 15H), 2.35–4.18 (m; 6H)

(2) (Hydrogenation of obtained reaction mixture)

20.0 g (111 mmol) of the obtained distillate was put into an electromagnetically stirred autoclave with a 300 mL internal volume and equipped with a gas introduction port and a sampling port, along with 80 mL of isopropyl alcohol and 2.0 g of Raney nickel (hydrogenation catalyst). The atmosphere on the inside was replaced with hydrogen gas, after which the temperature was raised to 80° C. while the pressure was held at approximately 8.0 atm (gauge pressure) by supplying hydrogen gas. A reaction was conducted for 2 hours while the temperature was kept at 80° C. The reaction was matured by raising the temperature to 100° C. and allowing the reaction to continue for another 4 hours. The pressure inside the autoclave was maintained at 8.0 atm (gauge pressure) by constantly supplying hydrogen gas during these reaction periods.

Upon completion of the reaction, the autoclave was cooled and the contents taken out, and the Raney nickel was removed by filtration to obtain a filtrate. This filtrate was analyzed by gas chromatography, which revealed that 14.7 g (85 mmol) of 5-(butylamino)-3-methyl-1-pentanol had been produced (77% yield based on the 2-(butylamino)-4-methyltetrahydropyran used).

Example 28

(1) (Reaction of 2-hydroxy-4-methyltetrahydrofuran and ammonia)

The atmosphere inside a glass three-necked flask with a 300 mL internal volume and equipped with a stirrer was replaced with nitrogen gas, after which 45 g (441 mmol) of 2-hydroxy-4-methyltetrahydrofuran was put in, and the temperature of the liquid on the inside was lowered to 2° C. by cooling in an ice-water bath. 90 g of a 25% aqueous ammonia solution (1324 mmol as ammonia, 3 times (molar) with respect to 2-hydroxy-4-methyltetrahydrofuran) was supplied dropwise into the liquid on the inside under agitation over a period of 10 minutes while the temperature of the liquid inside was maintained at 10° C. or lower. The system was stirred for another 30 minutes at 10° C. after completion of the dropping.

Upon completion of the stirring, the solution part of the reaction mixture thus obtained was analyzed by gas chromatography, which revealed that 11.6 g of the raw material 2-hydroxy-4-methyltetrahydrofuran (74% conversion).

(2) (Hydrogenation of obtained reaction mixture)

All of the obtained mixture (approximately 135 g) was put into an electromagnetically stirred autoclave with a 300 mL internal volume and equipped with a gas introduction port and a sampling port, along with 4.1 g of Raney nickel (hydrogenation catalyst). The atmosphere on the inside was replaced with hydrogen gas, after which the temperature was raised to 80° C. while the pressure was held at approximately 8.0 atm (gauge pressure) by supplying hydrogen gas. A reaction was conducted for 8 hours while the temperature was kept at 80° C. The pressure inside the autoclave was maintained at 8.0 atm (gauge pressure) by constantly supplying hydrogen gas during these reaction periods.

Upon completion of the reaction, the autoclave was cooled and the contents taken out, and the Raney nickel was removed by filtration to obtain a filtrate. This filtrate was analyzed by gas chromatography, which revealed that 36.9 g (358 mmol) of 4-amino-2-methyl-1-butanol had been produced (81% yield based on the 2-hydroxy-4-methyltetrahydrofuran used).

Manufacturing methods E and F illustrated in Examples 20 to 28 above allow an aminoalcohol classified as a primary or secondary amine, and in which hydroxyl group and amino group are linked by a main chain including four or five carbon atoms, to be manufactured at a high yield from raw materials that are readily available and easy to handle. Furthermore, no special reaction apparatus, special reaction conditions, or complicated after-treatment operation is required. Therefore, the present invention provides a method with which the above-mentioned aminoalcohol can be manufactured in advantageously in an industrial setting.

The entire disclosures of the specifications, claims, and summaries of Japanese Patent Application Nos. 11-219794, 11-219795, and 11-272146 filed on Aug. 3, 1999, Aug. 3, 1999, and Sep. 27, 1999, respectively, are hereby incorporated by reference.

What is claimed is:

1. A method for manufacturing an aminoalcohol expressed by Formula 3a

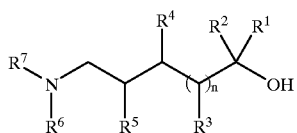

(3a)

where n is 0 or 1; $R^1$ and $R^2$ are each a hydrogen atom, a monovalent saturated hydrocarbon group which is optionally substituted, or a monovalent aromatic group which is optionally substituted, or $R^1$ and $R^2$ are bonded together into a divalent saturated hydrocarbon group which is optionally substituted; $R^3$, $R^4$, and $R^5$ are each a hydrogen atom, a monovalent saturated hydrocarbon group which is optionally substituted, or a monovalent aromatic group which is optionally substituted; and $R^6$ and $R^7$ are each a monovalent saturated hydrocarbon group which is optionally substituted or a monovalent aromatic group which is optionally substituted, or $R^6$ and $R^7$ are bonded together into a divalent saturated aliphatic group which is optionally substituted, which method comprises:

reacting a cyclic hemiacetal expressed by Formula 1

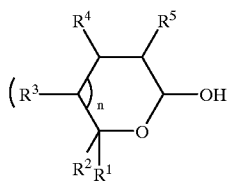

(1)

where n, $R^1$, $R^2$, $R^3$, $R^4$, and $R^5$ are defined the same as above
with hydrogen and a secondary amine expressed by Formula 2a

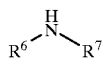

(2a)

where R and R are defined the same as above in the presence of a hydrogenation catalyst to obtain the aminoalcohol of Formula 3a.

2. A method for manufacturing an aminoalcohol expressed by Formula 3a

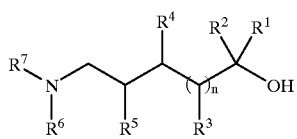

(3a)

where n is 0 or 1; $R^1$ and $R^2$ are each a hydrogen atom, a monovalent saturated hydrocarbon group which is optionally substituted, or a monovalent aromatic group which is optionally substituted, or $R^1$ and $R^2$ are bonded together into a divalent saturated hydrocarbon group which is optionally substituted; $R^3$, $R^4$, and $R^5$ are each a hydrogen atom, a monovalent saturated hydrocarbon group which is optionally substituted, or a monovalent aromatic group which is optionally substituted; and $R^6$ and $R^7$ are each a monovalent saturated hydrocarbon group which is optionally substituted or a monovalent aromatic group which is optionally substituted, or $R^6$ and $R^7$ are bonded together into a divalent saturated aliphatic group which is optionally substituted, which method comprises:

reacting a cyclic hemiacetal expressed by Formula 1

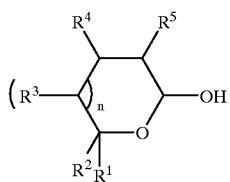

(1)

where n, $R^1$, $R^2$, $R^3$, $R^4$ and $R^5$ are defined the same as above with a secondary amine expressed by Formula 2a

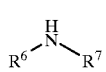

(2a)

where $R^6$ and $R^7$ are defined the same as above to obtain an aminoether expressed by Formula 4a

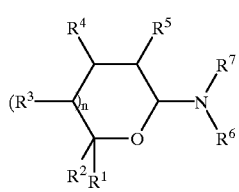

(4a)

where n, $R^1$, $R^2$, $R^3$, $R^4$, $R^5$, $R^6$ and $R^7$ are defined the same as above; and hydrogenating said aminoether to obtain the aminoalcohol of Formula 3a.

3. An aminoalcohol expressed by Formula 3a'

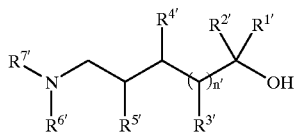
(3a')

where n' is 0 or 1; $R^{1'}$ and $R^{2'}$ are each a hydrogen atom, a monovalent saturated hydrocarbon group which is optionally substituted, or a monovalent aromatic group which is optionally substituted, or $R^{1'}$ and $R^{2'}$ are bonded together into a divalent saturated hydrocarbon group which is optionally substituted; $R^{3'}$ and $R^{5'}$ are each a hydrogen atom, a monovalent saturated hydrocarbon group which is optionally substituted, or a monovalent aromatic group which is optionally substituted; $R^{4'}$ is a monovalent saturated hydrocarbon group which is optionally substituted or a monovalent aromatic group which is optionally substituted; when n is 0, $R^{6'}$ and $R^{7'}$ are each a monovalent saturated hydrocarbon group which is optionally substituted or a monovalent aromatic group which is optionally substituted, and when n is 1, $R^{6'}$ is a monovalent saturated hydrocarbon group having one carbon atom or greater which group is optionally substituted or a monovalent aromatic group which is optionally substituted, and $R^{7'}$ is a monovalent saturated hydrocarbon group having two carbon atoms or greater which group is optionally substituted or a monovalent aromatic group which is optionally substituted, or $R^{6'}$ and $R^{7'}$ are bonded together into a divalent saturated aliphatic group which is optionally substituted.

4. An aminoalcohol expressed by Formula 4a

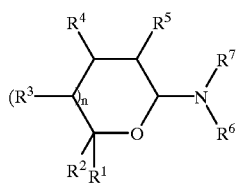
(4a)

where n is 0 or 1; $R^1$ and $R^2$ are each a hydrogen atom, a monovalent saturated hydrocarbon group which is optionally substituted, or a monovalent aromatic group which is optionally substituted, or $R^1$ and $R^2$ are bonded together into a divalent saturated hydrocarbon group which is optionally substituted; $R^3$, $R^4$, and $R^5$ are each a hydrogen atom, a monovalent saturated hydrocarbon group which is optionally substituted, or a monovalent aromatic group which is optionally substituted; and $R^6$ and $R^7$ are each a monovalent saturated hydrocarbon group which is optionally substituted or a monovalent aromatic group which is optionally substituted, or $R^6$ and $R^7$ are bonded together into a divalent saturated aliphatic group which is optionally substituted.

5. A method for manufacturing an aminoalcohol expressed by Formula 3b

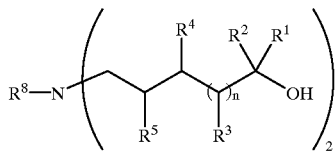
(3b)

where n is 0 or 1; $R^1$ and $R^2$ are each a hydrogen atom, a monovalent saturated hydrocarbon group which is optionally substituted, or a monovalent aromatic group which is optionally substituted, or $R^1$ and $R^2$ are bonded together into a divalent saturated hydrocarbon group which is optionally substituted; $R^3$, $R^4$, and $R^5$ are each a hydrogen atom, a monovalent saturated hydrocarbon group which is optionally substituted, or a monovalent aromatic group which is optionally substituted; and $R^6$ is a monovalent saturated hydrocarbon group which is optionally substituted or a monovalent aromatic group which is optionally substituted), which method comprises:

reacting a cyclic hemiacetal expressed by Formula 1

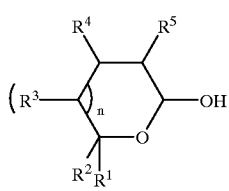
(1)

where n, $R^1$, $R^2$, $R^3$, $R^4$, and $R^5$ are defined the same as above with hydrogen and a primary amine expressed by Formula 2b $$R^8—NH_2 \quad (2b)$$

where $R^8$ is defined the same as above in the presence of a hydrogenation catalyst to obtain the aminoalcohol expressed by Formula 3b.

6. A method for manufacturing an aminoalcohol expressed by Formula 3b

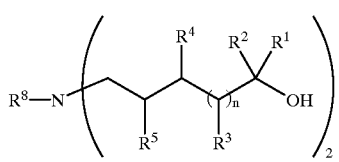
(3b)

where n is 0 or 1; $R^1$ and $R^2$ are each a hydrogen atom, a monovalent saturated hydrocarbon group which is optionally substituted, or a monovalent aromatic group which is optionally substituted, or $R^1$ and $R^2$ are bonded together into a divalent saturated hydrocarbon group which is optionally substituted; $R^3$, $R^4$, and $R^5$ are each a hydrogen atom, a monovalent saturated hydrocarbon group which is optionally substituted, or a monovalent aromatic group which is optionally substituted; and $R^8$ is a monovalent saturated hydrocarbon group which is optionally substituted or a monovalent aromatic group which is optionally substituted, which method comprises:

reacting a cyclic hemiacetal expressed by Formula 1

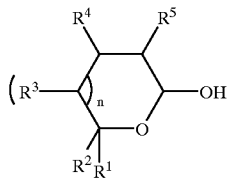

(1)

where n, $R^1$, $R^2$, $R^3$, $R^4$ and $R^5$ are defined the same as above with a primary amine expressed by Formula 2b

(2b)

where $R^8$ is defined the same as above; and subjecting the reaction mixture thus obtained to hydrogenation reaction to obtain the aminoalcohol of Formula 3b.

7. An aminoalcohol expressed by Formula 3b

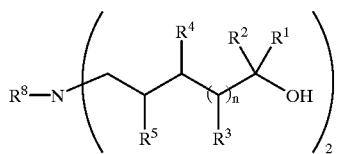

(3b)

where n is 0 or 1; $R^1$ and $R^2$ are each a hydrogen atom, a monovalent saturated hydrocarbon group which is optionally substituted, or a monovalent aromatic group which is optionally substituted, or $R^1$ and $R^2$ are bonded together into a divalent saturated hydrocarbon group which is optionally substituted; $R^3$, $R^4$, and $R^5$ are each a hydrogen atom, a monovalent saturated hydrocarbon group which is optionally substituted, or a monovalent aromatic group which is optionally substituted; and $R^8$ is a monovalent saturated hydrocarbon group which is optionally substituted or a monovalent aromatic group which is optionally substituted.

8. A method for manufacturing an aminoalcohol expressed by Formula 3c

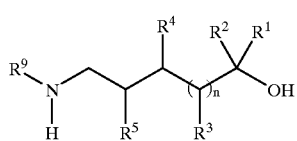

(3c)

where n is 0 or 1; $R^1$ and $R^2$ are each a hydrogen atom, a monovalent saturated hydrocarbon group which is optionally substituted, or a monovalent aromatic group which is optionally substituted, or $R^1$ and $R^2$ are bonded together into a divalent saturated hydrocarbon group which is optionally substituted; $R^3$, $R^4$, and $R^5$ are each a hydrogen atom, a monovalent saturated hydrocarbon group which is optionally substituted, or a monovalent aromatic group which is optionally substituted, and $R^9$ is a hydrogen atom, a monovalent saturated hydrocarbon group which is optionally substituted or a monovalent aromatic group which is optionally substituted, which method comprises:

reacting a cyclic hemiacetal expressed by Formula 1

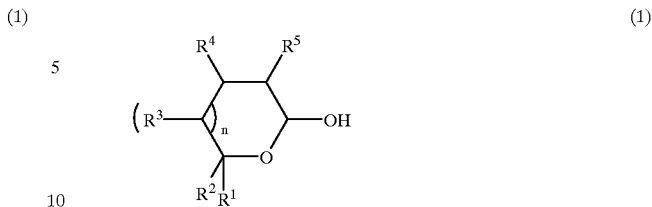

(1)

where n, $R^1$, $R^2$, $R^3$, $R^4$ and $R^5$ are defined the same as above,
with hydrogen and a nitrogen-containing compound expressed by Formula 2c

(2c)

where $R^9$ is defined the same as above, in the presence of a hydrogenation catalyst to obtain the aminoalcohol expressed by Formula 3c.

9. A method according to claim 8, which method comprises:

reacting a cyclic hemiacetal expressed by Formula 1'

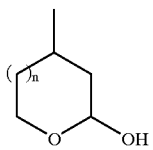

(1')

where n is 0 or 1;
with hydrogen and a nitrogen-containing compound expressed by Formula 2c

(2c)

where R is a hydrogen atom, a monovalent saturated hydrocarbon group which is optionally substituted, or a monovalent aromatic group which is optionally substituted in the presence of a hydrogenation catalyst to obtain an aminoalcohol expressed by Formula 3c'

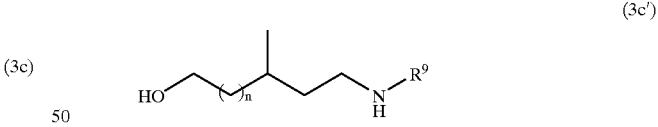

(3c')

where n and $R^9$ are defined the same as above.

10. A method for manufacturing an aminoalcohol expressed by Formula 3c

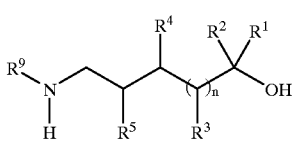

(3c)

where n is 0 or 1; $R^1$ and $R^2$ are each a hydrogen atom, a monovalent saturated hydrocarbon group which is optionally substituted, or a monovalent aromatic group which is optionally substituted, or $R^1$ and $R^2$ are bonded together into a divalent saturated hydrocarbon group which is optionally substituted; $R^3$, $R^4$, and $R^5$ are each a hydrogen atom, a monovalent saturated hydrocarbon group which is optionally substituted, or a monovalent aromatic group which is optionally substituted, and $R^9$ is a hydrogen atom, a monovalent saturated hydrocarbon group which is optionally substituted or a monovalent aromatic group which is optionally substituted, which method comprises:

reacting a cyclic hemiacetal expressed by Formula 1

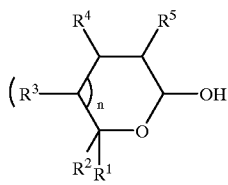

(1)

wherein, n, $R^1$, $R^2$, $R^3$, $R^4$ and $R^5$ are defined the same as above,
with a nitrogen-containing compound expressed by Formula 2c $$R^9-NH_2 \qquad (2c)$$

where $R^9$ is defined the same as above; and
subjecting the reaction mixture thus obtained to reaction with hydrogen in the presence of a hydrogenation catalyst to obtain the aminoalcohol expressed by Formula 3c.

11. A method according to claim 10, which method comprises:

reacting a cyclic hemiacetal expressed by Formula 1'

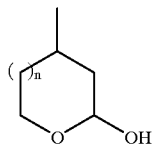

(1')

where n is 0 or 1
with a nitrogen-containing compound expressed by Formula 2c $$R^9-NH2 \qquad (2c)$$

where $R^9$ is a hydrogen atom, a monovalent saturated hydrocarbon group which is optionally substituted, or a monovalent aromatic group which is optionally substituted; and subjecting the reaction mixture thus obtained to reaction with hydrogen in the presence of a hydrogenation catalyst to obtain an aminoalcohol expressed by Formula 3c'

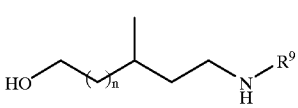

(3c')

where n and $R^9$ are defined the same as above.

12. The manufacturing method according to any one of claims 8 to 11, wherein the nitrogen-containing compound is used in an amount of 0.9 to 50 moles per mole of the cyclic hemiacetal.

13. The manufacturing method according to any one of claims 8 to 11, wherein the nitrogen-containing compound is used in an amount of 1 to 20 moles per mole of the cyclic hemiacetal.

14. The manufacturing method according to any one of claims 9 and 11, wherein the cyclic hemiacetal expressed by Formula 1' is produced by reacting an alkenol compound expressed by Formula 5'

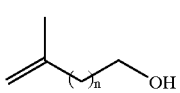

(5')

where n is defined the same as above with hydrogen and carbon monoxide in the presence of a rhodium compound and a tertiary organophosphorus compound.

15. An aminoalcohol expressed by Formula 3c"

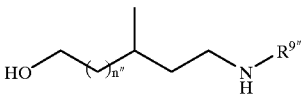

(3c")

where n" is 0 or 1, $R^{9"}$ is a hydrogen atom or a methyl group when n" is 1, and $R^{9"}$ is a methyl group when n" is 0.

* * * * *